(12) United States Patent
Chanduszko et al.

(10) Patent No.: US 7,666,203 B2
(45) Date of Patent: Feb. 23, 2010

(54) TRANSSEPTAL PUNCTURE APPARATUS

(75) Inventors: Andrzej J. Chanduszko, Weymouth, MA (US); Carol A. Devellian, Topsfield, MA (US)

(73) Assignee: NMT Medical, Inc., Boston, MA (US)

( * ) Notice: Subject to any disclaimer, the term of this patent is extended or adjusted under 35 U.S.C. 154(b) by 0 days.

(21) Appl. No.: 10/841,695

(22) Filed: May 7, 2004

(65) Prior Publication Data

US 2005/0101984 A1 May 12, 2005

Related U.S. Application Data

(60) Provisional application No. 60/517,983, filed on Nov. 6, 2003.

(51) Int. Cl.
*A61B 17/34* (2006.01)

(52) U.S. Cl. ...................... 606/185; 128/898

(58) Field of Classification Search ........... 606/185, 606/213, 151, 41; 600/411; 604/96.01; 128/898
See application file for complete search history.

(56) References Cited

U.S. PATENT DOCUMENTS

| | | | |
|---|---|---|---|
| 3,077,733 A | 2/1963 | Axe et al. | |
| 3,103,666 A | 9/1963 | Bone | |
| 3,470,834 A | 10/1969 | Bone | |
| 3,716,058 A | 2/1973 | Tanner, Jr. | |
| 3,874,388 A | 4/1975 | King et al. | 128/334 R |
| 3,875,648 A | 4/1975 | Bone | |
| 3,990,619 A | 11/1976 | Russell | |
| 4,006,747 A | 2/1977 | Kronenthal et al. | |
| 4,007,743 A | 2/1977 | Blake | 128/334 R |
| 4,039,078 A | 8/1977 | Bone | |
| 4,235,238 A | 11/1980 | Ogiu et al. | |
| 4,394,864 A | 7/1983 | Sandhaus | |
| 4,425,908 A | 1/1984 | Simon | |
| 4,485,816 A | 12/1984 | Krumme | |
| 4,515,583 A | 5/1985 | Sorich | |
| 4,556,050 A | 12/1985 | Hodgson | |
| 4,586,502 A | 5/1986 | Bedi et al. | |
| 4,669,473 A | 6/1987 | Richards et al. | |
| 4,696,300 A | 9/1987 | Anderson | |

(Continued)

FOREIGN PATENT DOCUMENTS

EP 0553259 8/1993

(Continued)

OTHER PUBLICATIONS

International Search Report for International Application No. PCT/US2004/014296, dated Sep. 24, 2004 (6 pages).

(Continued)

*Primary Examiner*—Anhtuan T Nguyen
*Assistant Examiner*—Tuan V Nguyen
(74) *Attorney, Agent, or Firm*—Finnegan, Henderson, Farabow, Garrett & Dunner LLP

(57) ABSTRACT

Devices and methods for performing a transeptal puncture procedure are described. In certain embodiments, the device includes a blunt outer needle, and a second inner needle disposed longitudinally through the lumen of the outer needle, wherein the inner needle is flexible, e.g., has a flexible portion and/or a bend or other non-traumatic conformation at its tip.

5 Claims, 16 Drawing Sheets

U.S. PATENT DOCUMENTS

| | | | |
|---|---|---|---|
| 4,705,040 A | 11/1987 | Mueller et al. | |
| 4,799,483 A | 1/1989 | Kraff | |
| 4,800,890 A | 1/1989 | Cramer | |
| 4,834,096 A | 5/1989 | Oh et al. | |
| 4,836,204 A | 6/1989 | Landymore et al. | 128/334 R |
| 4,844,066 A | 7/1989 | Stein | |
| 4,915,107 A | 4/1990 | Rebuffat et al. | |
| 4,985,014 A | 1/1991 | Orejola | |
| 5,021,059 A | 6/1991 | Kensey et al. | |
| 5,030,199 A | 7/1991 | Barwick et al. | |
| 5,037,433 A | 8/1991 | Wilk et al. | |
| 5,041,129 A | 8/1991 | Hayhurst et al. | 606/232 |
| 5,042,976 A | 8/1991 | Ishitsu et al. | |
| 5,049,153 A | 9/1991 | Nakao et al. | |
| 5,057,114 A | 10/1991 | Wittich et al. | 606/127 |
| 5,073,166 A | 12/1991 | Parks et al. | |
| 5,108,420 A | 4/1992 | Marks | 606/213 |
| 5,112,310 A | 5/1992 | Grobe | |
| 5,171,259 A | 12/1992 | Inoue | |
| 5,190,528 A | 3/1993 | Fonger et al. | |
| 5,192,301 A | 3/1993 | Kamiya et al. | 606/213 |
| 5,222,974 A | 6/1993 | Kensey et al. | |
| 5,236,440 A | 8/1993 | Hlavacek | |
| 5,257,637 A | 11/1993 | El Gazayerli | |
| 5,282,827 A | 2/1994 | Kensey et al. | |
| 5,284,488 A | 2/1994 | Sideris | 606/213 |
| 5,304,184 A | 4/1994 | Hathaway et al. | |
| 5,304,185 A | 4/1994 | Taylor | |
| 5,312,341 A | 5/1994 | Turi | |
| 5,312,435 A | 5/1994 | Nash et al. | |
| 5,320,633 A | 6/1994 | Allen et al. | |
| 5,334,217 A | 8/1994 | Das | 606/213 |
| 5,336,252 A | 8/1994 | Cohen | |
| 5,354,308 A | 10/1994 | Simon et al. | |
| 5,357,979 A | 10/1994 | Imran | 128/772 |
| 5,370,661 A | 12/1994 | Branch | |
| 5,403,338 A | 4/1995 | Milo | |
| 5,411,481 A | 5/1995 | Allen et al. | |
| 5,413,584 A | 5/1995 | Schulze | |
| 5,417,699 A | 5/1995 | Klein et al. | |
| 5,417,700 A | 5/1995 | Egan | |
| 5,425,744 A | 6/1995 | Fagan et al. | 606/213 |
| 5,433,727 A | 7/1995 | Sideris | 606/213 |
| 5,451,235 A | 9/1995 | Lock et al. | 606/213 |
| 5,478,353 A | 12/1995 | Yoon | |
| 5,486,185 A | 1/1996 | Freitas et al. | |
| 5,486,193 A | 1/1996 | Bourne et al. | 606/194 |
| 5,507,811 A | 4/1996 | Koike et al. | |
| 5,540,712 A | 7/1996 | Kleshinski et al. | 606/198 |
| 5,545,138 A | 8/1996 | Fugoso et al. | 604/102 |
| 5,573,542 A | 11/1996 | Stevens | |
| 5,577,299 A | 11/1996 | Thompson et al. | 24/131 C |
| 5,578,045 A | 11/1996 | Das | 606/151 |
| 5,597,378 A | 1/1997 | Jervis | |
| 5,601,571 A | 2/1997 | Moss | |
| 5,601,575 A | 2/1997 | Measamee et al. | |
| 5,618,311 A | 4/1997 | Gryskiewicz | |
| 5,620,461 A | 4/1997 | Muijs Van De Moer et al. | 606/213 |
| 5,634,936 A | 6/1997 | Linden et al. | 606/213 |
| 5,649,959 A | 7/1997 | Hannam et al. | |
| 5,683,411 A | 11/1997 | Kavteladze et al. | 606/200 |
| 5,702,421 A | 12/1997 | Schneidt | 606/213 |
| 5,709,707 A | 1/1998 | Lock et al. | 606/213 |
| 5,713,952 A | 2/1998 | Vanney et al. | |
| 5,720,754 A | 2/1998 | Middleman et al. | |
| 5,725,552 A | 3/1998 | Kotula et al. | 606/213 |
| 5,733,294 A | 3/1998 | Forber et al. | 606/151 |
| 5,733,337 A | 3/1998 | Carr, Jr. et al. | |
| 5,741,297 A | 4/1998 | Simon | 606/213 |
| 5,746,765 A | 5/1998 | Kleshinski et al. | 606/198 |
| 5,749,895 A | 5/1998 | Sawyer et al. | |
| 5,776,162 A | 7/1998 | Kleshinski et al. | |
| 5,797,960 A | 8/1998 | Stevens et al. | |
| 5,800,516 A | 9/1998 | Fine et al. | 623/1 |
| 5,810,848 A | 9/1998 | Hayhurst | |
| 5,810,884 A | 9/1998 | Kim | 606/213 |
| 5,823,956 A | 10/1998 | Roth et al. | |
| 5,827,216 A | 10/1998 | Igo et al. | |
| 5,829,447 A | 11/1998 | Stevens et al. | |
| 5,836,311 A | 11/1998 | Borst et al. | |
| 5,853,422 A | 12/1998 | Huebsch et al. | 606/213 |
| 5,855,614 A | 1/1999 | Stevens et al. | |
| 5,861,003 A | 1/1999 | Latson et al. | 606/213 |
| 5,868,753 A | 2/1999 | Schatz | 606/108 |
| 5,879,366 A | 3/1999 | Shaw et al. | 606/213 |
| 5,885,238 A | 3/1999 | Stevens et al. | |
| 5,893,856 A | 4/1999 | Jacob et al. | |
| 5,895,404 A | 4/1999 | Ruiz | |
| 5,902,317 A | 5/1999 | Kleshinski et al. | 606/198 |
| 5,902,319 A | 5/1999 | Daley | |
| 5,904,703 A | 5/1999 | Gilson | |
| 5,919,200 A * | 7/1999 | Stambaugh et al. | 606/159 |
| 5,924,424 A | 7/1999 | Stevens et al. | |
| 5,927,284 A | 7/1999 | Borst et al. | |
| 5,928,250 A * | 7/1999 | Koike et al. | 606/139 |
| 5,935,108 A * | 8/1999 | Katoh et al. | 604/164.11 |
| 5,944,738 A | 8/1999 | Amplatz et al. | 606/213 |
| 5,964,782 A | 10/1999 | Lafontaine et al. | |
| 5,976,174 A | 11/1999 | Ruiz | 606/213 |
| 5,989,268 A | 11/1999 | Pugsley, Jr. et al. | |
| 5,993,475 A | 11/1999 | Lin et al. | 606/213 |
| 5,997,556 A | 12/1999 | Tanner | |
| 5,997,562 A | 12/1999 | Zadno-Azizi et al. | 606/194 |
| 6,001,085 A | 12/1999 | Lurie et al. | |
| 6,007,558 A | 12/1999 | Ravenscroft et al. | 606/200 |
| 6,010,517 A | 1/2000 | Baccaro | |
| 6,015,378 A | 1/2000 | Borst et al. | |
| 6,024,756 A | 2/2000 | Huebsch et al. | 606/213 |
| 6,030,007 A | 2/2000 | Bassily et al. | 289/1.5 |
| 6,030,405 A | 2/2000 | Zarbatany et al. | 606/191 |
| 6,056,760 A | 5/2000 | Koike et al. | |
| 6,077,291 A | 6/2000 | Das | 606/213 |
| 6,079,414 A | 6/2000 | Roth | |
| 6,080,182 A | 6/2000 | Shaw et al. | 606/213 |
| 6,086,610 A | 7/2000 | Duerig et al. | 623/1 |
| 6,113,609 A | 9/2000 | Adams | 606/139 |
| 6,117,159 A | 9/2000 | Huebsch et al. | 606/213 |
| 6,129,755 A | 10/2000 | Mathis et al. | 623/1.15 |
| 6,132,438 A | 10/2000 | Fleischman et al. | |
| 6,142,975 A | 11/2000 | Jalisi et al. | |
| 6,149,664 A | 11/2000 | Kurz | 606/194 |
| 6,152,918 A | 11/2000 | Padilla et al. | |
| 6,162,195 A | 12/2000 | Igo et al. | |
| 6,165,183 A | 12/2000 | Kuehn et al. | |
| 6,165,204 A | 12/2000 | Levinson et al. | |
| 6,171,329 B1 | 1/2001 | Shaw et al. | 606/213 |
| 6,174,322 B1 * | 1/2001 | Schneidt | 606/213 |
| 6,206,895 B1 | 3/2001 | Levinson | |
| 6,206,907 B1 | 3/2001 | Marino et al. | 606/215 |
| 6,206,912 B1 * | 3/2001 | Goldsteen et al. | 623/1.23 |
| 6,206,921 B1 | 3/2001 | Guagliano et al. | 606/215 |
| 6,214,029 B1 | 4/2001 | Thill et al. | 606/213 |
| 6,217,590 B1 | 4/2001 | Levinson | |
| 6,221,092 B1 | 4/2001 | Koike et al. | 606/213 |
| 6,228,097 B1 | 5/2001 | Levinson et al. | |
| 6,231,561 B1 | 5/2001 | Frazier et al. | |
| 6,245,080 B1 | 6/2001 | Levinson | |
| 6,254,550 B1 | 7/2001 | McNamara et al. | |
| 6,258,026 B1 | 7/2001 | Ravenscroft et al. | |
| 6,270,515 B1 | 8/2001 | Linden et al. | 606/213 |
| 6,277,138 B1 | 8/2001 | Levinson et al. | |
| 6,278,139 B1 | 8/2001 | Levinson et al. | |
| 6,278,371 B1 | 8/2001 | Hopkins | |

| | | |
|---|---|---|
| 6,287,317 B1 | 9/2001 | Makower et al. |
| 6,290,674 B1 | 9/2001 | Roue et al. |
| 6,302,903 B1 | 10/2001 | Mulier et al. |
| 6,306,150 B1 | 10/2001 | Levinson |
| 6,312,446 B1 | 11/2001 | Huebsch et al. ............. 606/213 |
| 6,319,263 B1 | 11/2001 | Levinson |
| 6,322,548 B1 | 11/2001 | Payne et al. |
| 6,325,807 B1 | 12/2001 | Que |
| 6,332,877 B1 | 12/2001 | Michels |
| 6,334,872 B1 | 1/2002 | Termin et al. |
| 6,336,898 B1 | 1/2002 | Borst et al. |
| 6,342,064 B1 | 1/2002 | Koike et al. ................. 606/213 |
| 6,344,049 B1 | 2/2002 | Levinson |
| 6,346,074 B1 | 2/2002 | Roth ........................... 600/121 |
| 6,348,041 B1 | 2/2002 | Klint |
| 6,348,059 B1 | 2/2002 | Hathaway et al. |
| 6,350,229 B1 | 2/2002 | Borst et al. |
| 6,352,531 B1 | 3/2002 | O'Connor et al. ............. 606/15 |
| 6,352,552 B1 | 3/2002 | Levinson et al. |
| 6,355,052 B1 | 3/2002 | Neuss et al. ................. 606/213 |
| 6,364,826 B1 | 4/2002 | Borst et al. |
| 6,364,846 B1 | 4/2002 | Nakamura |
| 6,364,853 B1 | 4/2002 | French et al. |
| 6,364,876 B1 | 4/2002 | Erb et al. |
| 6,371,906 B1 | 4/2002 | Borst et al. |
| 6,371,971 B1 | 4/2002 | Tsugita et al. |
| 6,375,625 B1 | 4/2002 | French et al. |
| 6,375,671 B1 | 4/2002 | Kobayashi et al. ........... 606/213 |
| 6,379,342 B1 | 4/2002 | Levinson |
| 6,379,368 B1 | 4/2002 | Corcoran et al. ............. 606/153 |
| 6,387,104 B1 | 5/2002 | Pugsley, Jr. et al. ......... 606/139 |
| 6,394,948 B1 | 5/2002 | Borst et al. |
| 6,398,796 B2 | 6/2002 | Levinson |
| 6,402,772 B1 | 6/2002 | Amplatz et al. ............. 606/200 |
| 6,440,152 B1 | 8/2002 | Gainor et al. ................. 606/213 |
| 6,458,100 B2 | 10/2002 | Roue et al. |
| 6,460,749 B1 | 10/2002 | Levinson et al. |
| 6,464,629 B1 | 10/2002 | Boone et al. |
| 6,464,630 B1 | 10/2002 | Borst et al. |
| 6,482,210 B1 | 11/2002 | Skiba et al. |
| 6,482,224 B1 | 11/2002 | Michler et al. ............. 606/219 |
| 6,488,706 B1 | 12/2002 | Solymar |
| 6,494,888 B1 | 12/2002 | Laufer et al. ................. 606/153 |
| 6,527,786 B1 | 3/2003 | Davis et al. |
| 6,537,198 B1 | 3/2003 | Vidlund et al. |
| 6,544,274 B2 | 4/2003 | Danitz et al. |
| 6,551,344 B2 | 4/2003 | Thill ........................... 606/213 |
| 6,572,593 B1 | 6/2003 | Daum |
| 6,596,013 B2 | 7/2003 | Yang et al. ................... 606/215 |
| 6,606,513 B2 * | 8/2003 | Lardo et al. ................. 600/411 |
| 6,623,508 B2 | 9/2003 | Shaw et al. .................. 606/213 |
| 6,623,518 B2 | 9/2003 | Thompson et al. ......... 623/1.11 |
| RE38,335 E | 11/2003 | Aust et al. |
| 6,650,923 B1 * | 11/2003 | Lesh et al. .................. 600/407 |
| 6,652,486 B2 | 11/2003 | Bialecki et al. |
| 6,663,592 B2 | 12/2003 | Rhad et al. |
| 6,685,724 B1 | 2/2004 | Haluck |
| 6,692,471 B2 | 2/2004 | Boudreaux |
| 6,702,835 B2 | 3/2004 | Ginn |
| 6,712,804 B2 | 3/2004 | Roue et al. ................... 604/500 |
| 6,712,836 B1 | 3/2004 | Berg et al. ................... 606/213 |
| 6,730,062 B2 | 5/2004 | Hoffman et al. |
| 6,730,081 B1 * | 5/2004 | Desai ........................... 606/40 |
| 6,855,124 B1 * | 2/2005 | Gonzalez et al. ......... 604/96.01 |
| 6,939,348 B2 * | 9/2005 | Malecki et al. ............. 606/41 |
| 7,220,265 B2 | 5/2007 | Chanduszko et al. |
| 2001/0014800 A1 | 8/2001 | Frazier et al. |
| 2001/0034537 A1 | 10/2001 | Shaw et al. |
| 2001/0037129 A1 | 11/2001 | Thill ........................... 606/213 |
| 2001/0039435 A1 | 11/2001 | Roue et al. |
| 2001/0044639 A1 | 11/2001 | Levinson |
| 2001/0049492 A1 | 12/2001 | Frazier et al. |
| 2002/0002373 A1 | 1/2002 | Boehlke et al. |
| 2002/0010481 A1 | 1/2002 | Jayaraman |
| 2002/0019648 A1 | 2/2002 | Akerfeldt et al. ............. 606/213 |
| 2002/0026094 A1 | 2/2002 | Roth |
| 2002/0026208 A1 | 2/2002 | Roe et al. ..................... 606/190 |
| 2002/0029048 A1 | 3/2002 | Miller |
| 2002/0032462 A1 | 3/2002 | Houser et al. |
| 2002/0043307 A1 | 4/2002 | Ishida et al. |
| 2002/0045908 A1 | 4/2002 | Nobles et al. |
| 2002/0052572 A1 | 5/2002 | Franco et al. .................. 604/8 |
| 2002/0077555 A1 | 6/2002 | Schwartz ..................... 600/486 |
| 2002/0096183 A1 | 7/2002 | Stevens et al. ............... 128/898 |
| 2002/0099389 A1 | 7/2002 | Michler et al. ............. 606/139 |
| 2002/0107531 A1 | 8/2002 | Schreck et al. ............. 606/142 |
| 2002/0120323 A1 | 8/2002 | Thompson et al. ......... 623/1.11 |
| 2002/0128680 A1 | 9/2002 | Pavlovic ..................... 606/200 |
| 2002/0129819 A1 | 9/2002 | Feldman et al. |
| 2002/0169377 A1 | 11/2002 | Khairkhahan et al. |
| 2002/0183786 A1 | 12/2002 | Girton ......................... 606/213 |
| 2002/0183787 A1 | 12/2002 | Wahr et al. .................. 606/213 |
| 2003/0028213 A1 | 2/2003 | Thill et al. .................. 606/200 |
| 2003/0045893 A1 | 3/2003 | Ginn |
| 2003/0050665 A1 | 3/2003 | Ginn |
| 2003/0059640 A1 | 3/2003 | Marton et al. ............... 428/544 |
| 2003/0100920 A1 | 5/2003 | Akin et al. ................... 606/213 |
| 2003/0139819 A1 | 7/2003 | Beer et al. ................... 623/23 |
| 2003/0144694 A1 | 7/2003 | Chanduszko et al. |
| 2003/0167055 A1 | 9/2003 | Kolata et al. |
| 2003/0181937 A1 | 9/2003 | Osterlind |
| 2003/0191494 A1 | 10/2003 | Gray et al. |
| 2003/0195530 A1 | 10/2003 | Thill ........................... 606/151 |
| 2003/0195531 A1 | 10/2003 | Gardiner et al. |
| 2003/0208232 A1 | 11/2003 | Blaeser et al. ............... 606/213 |
| 2003/0212435 A1 | 11/2003 | Gold et al. |
| 2004/0092973 A1 * | 5/2004 | Chanduszko et al. ........ 606/151 |
| 2004/0138701 A1 | 7/2004 | Haluck |
| 2004/0193147 A1 | 9/2004 | Malecki et al. |
| 2004/0230185 A1 | 11/2004 | Malecki et al. |
| 2004/0243122 A1 | 12/2004 | Auth et al. |
| 2004/0267191 A1 | 12/2004 | Gifford, III et al. |
| 2005/0021016 A1 | 1/2005 | Malecki et al. |
| 2005/0034735 A1 | 2/2005 | Deem et al. |
| 2005/0059984 A1 | 3/2005 | Chanduszko et al. |
| 2005/0065507 A1 * | 3/2005 | Hartley et al. ................. 606/41 |
| 2005/0080406 A1 | 4/2005 | Malecki et al. |
| 2005/0101984 A1 | 5/2005 | Chanduszko et al. |
| 2005/0119675 A1 * | 6/2005 | Adams et al. ............... 606/151 |
| 2005/0131401 A1 | 6/2005 | Malecki et al. |
| 2005/0131460 A1 | 6/2005 | Gifford, III et al. |
| 2006/0027241 A1 | 2/2006 | Malecki et al. |
| 2006/0074410 A1 | 4/2006 | Malecki et al. |

FOREIGN PATENT DOCUMENTS

| | | |
|---|---|---|
| EP | 1 013 227 | 6/2000 |
| EP | 1046375 A1 | 10/2000 |
| EP | 0 724 406 B1 | 12/2001 |
| EP | 1222897 | 7/2002 |
| WO | WO 92/06733 | 4/1992 |
| WO | WO 95/10983 | 4/1995 |
| WO | WO 95/13111 | 5/1995 |
| WO | WO 98/07375 | 2/1998 |
| WO | WO 99/18862 | 4/1999 |
| WO | WO 99/18864 | 4/1999 |
| WO | WO 99/18870 | 4/1999 |
| WO | WO 99/18871 | 4/1999 |
| WO | 99/25254 | 5/1999 |
| WO | 00/27292 | 5/2000 |
| WO | 01/49185 | 7/2001 |
| WO | WO 01/78596 | 10/2001 |
| WO | WO 02/41790 | 5/2002 |
| WO | WO 03/022159 | 3/2003 |
| WO | 03/059152 A2 | 7/2003 |
| WO | WO 03/077733 | 9/2003 |

| | | |
|---|---|---|
| WO | WO 03/088818 | 10/2003 |
| WO | WO 2004/028348 | 4/2004 |

OTHER PUBLICATIONS

National Aeronautics and Space Administration, "55-Nitinol-the Alloy with a Memory: Its Physical Metallurgy, Properties, and Applications," *A-Report*, 24-25.

Kimura et al., "Effects of Neutron Irradiation on the Transformation Behavior in Ti-Ni Alloys," Abstract, *Proceedings of the Int'l Conf. On Mariensitic Transformations* (1992) 935-940.

Ramanathan et al., "Experimental and Computational Methods for Shape Memory Alloys," *15th ASCE Engineering Mechanics Conf.* (Jun. 2-5, 2002) 12 pages.

Shabalovskaya, "Surface, corrosion and biocompatibility aspects of Nitinol as an implant material," *Bio-Medical Materials and Engineering*, (2002) 12:69-109.

Uchil, "Shape Memory Alloys-Characterization Techniques," *Pramana-Journal of Physics*, (2002) 58(5-6):1131-1139.

Hansen (June) Metals that Remember, Science 81:44-47.

Hawkins Jr., I. F., et al. (1987) The Puncture Needle as Guidewire: Needle Guide Technique for Percutaneous Nephrostomy, Seminars in Interventional Radiology 4(2): 126-130.

Kotan, C. et al. (2001) Diameter and Pressure of the Water-Jet for Liver Resection, Easter J. Med., 6(2):43-47.

Kramer PFO and Stroke: The Hidden Connection press release from http://www.evtoday.com/03_archive/0903/101.html, printed on Jun. 7, 2004.

Protsenko, J. A., Electrosurgical Tissue Resection: a Numerical and Experimental Study, Proceedings of SPIE, vol. 4954.

Ruiz, C.E. et al. (2001) The Puncture Technique: A New Method for Transcatheter Closure of Patent Foramen Ovale, Catheter and Cardiovasc. Interv. 53:369-372.

Stöckel, "Nitinol Medical Devices and Implants," *SMST-2000: Proceedings of the International Conference on Shape Memory and Superelastic Technologies*, 531-540.

Szili-Torok, T. et al. (2001) Transseptal Left Heart Catherisation Guided by Intracardiac Echocardiography, Heart 86:e11.

Written Opinion of the International Searching Authority for PCT/US2004/014296, mailed Sep. 24, 2004.

De Ponti, R. et al., "Trans-septal Catheterization for Radiofrequency Catheter Ablation of Cardiac Arrhythmias. Results and Safety of a Simplified Method," European Heart Journal, vol. 19, Jun. 1998, pp. 943-950.

"Elastic Deployment," SMST-2000 Proceedings of the International Conference on Shape Memory and Superelastic Technologies, Apr. 30 to May 4, 2000, Asilomar Conference Center, 3 pages.

Sommer, R.J. M.D., et al., "New Transseptal Puncture Technique for Transcatheter Closure of Patent Foramen Ovale," Mount Sinai Medical Center, New York, New York, publication date unknown but believed to be Jun. 2002 or earlier.

* cited by examiner

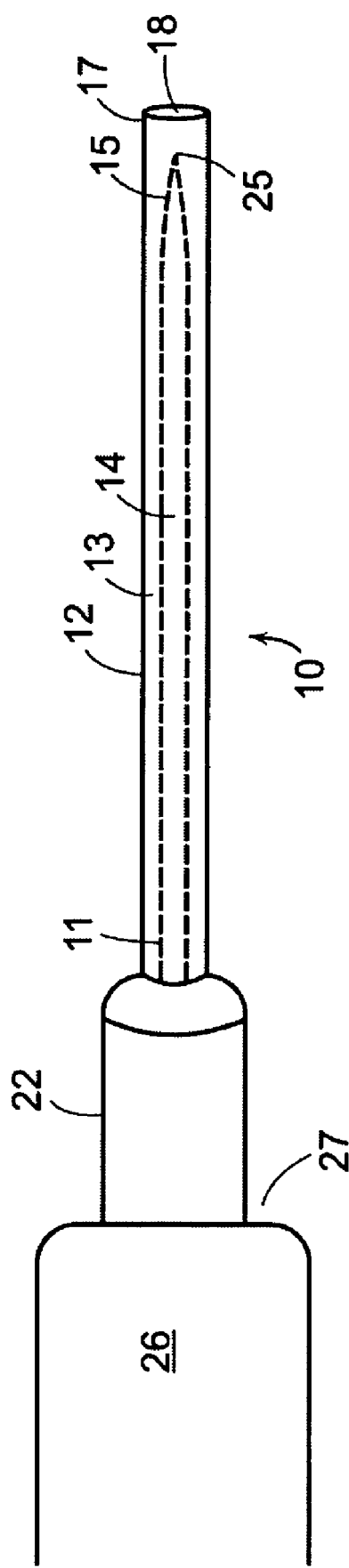
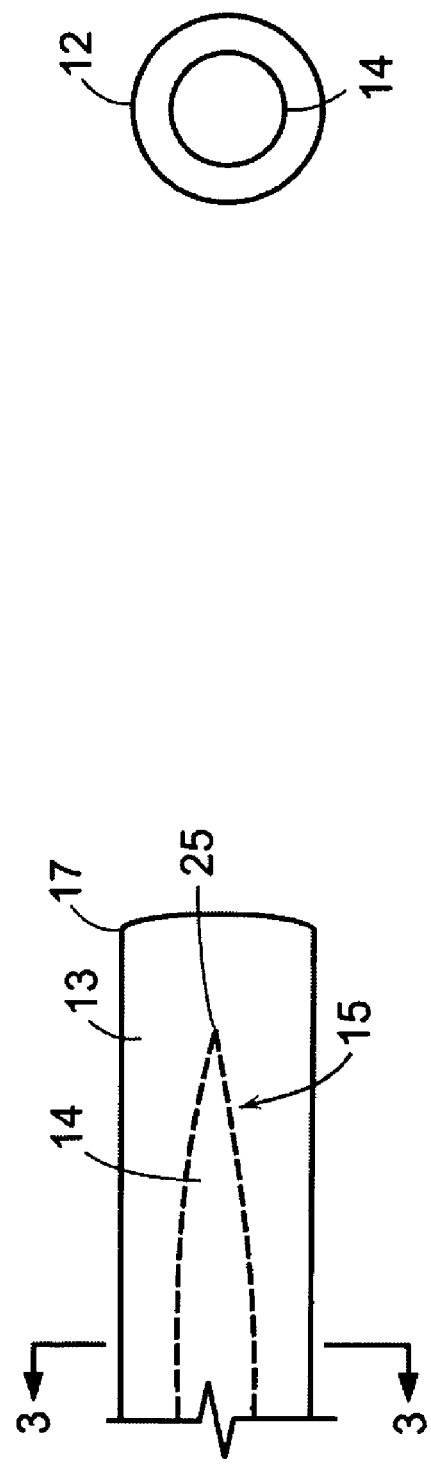
FIG. 1
FIG. 2
FIG. 3

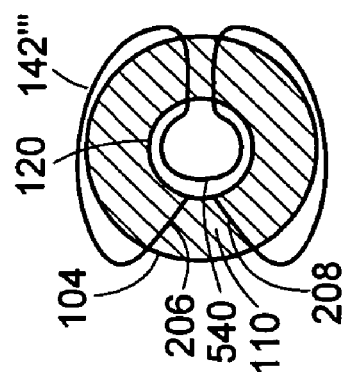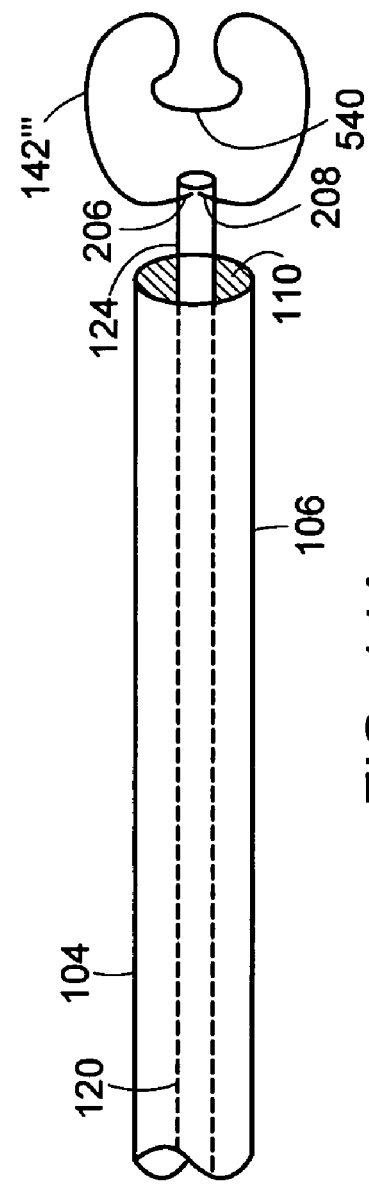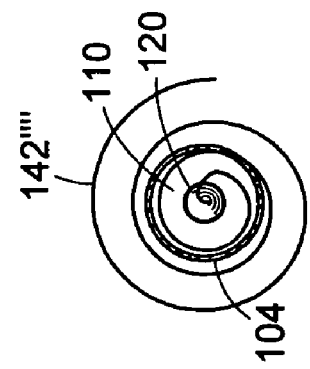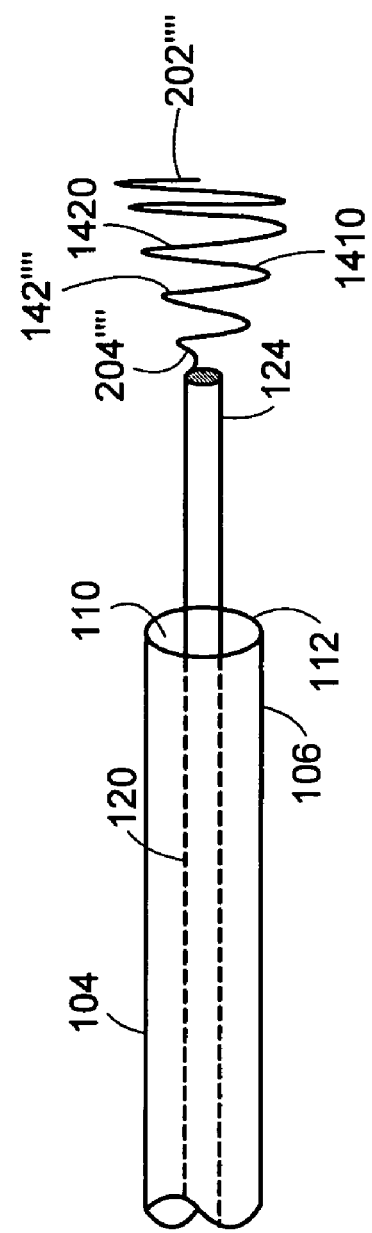

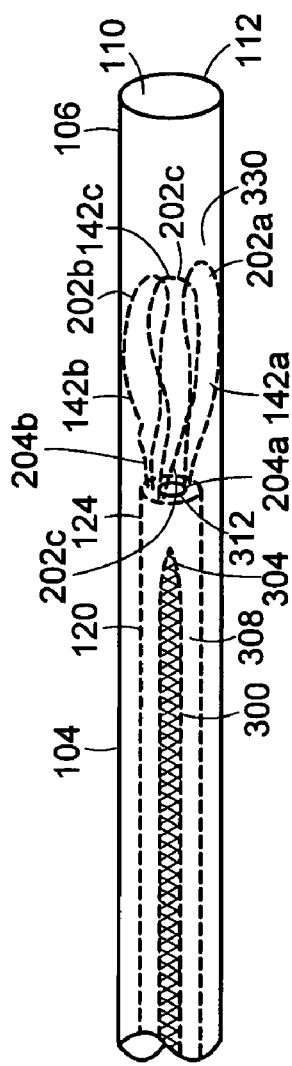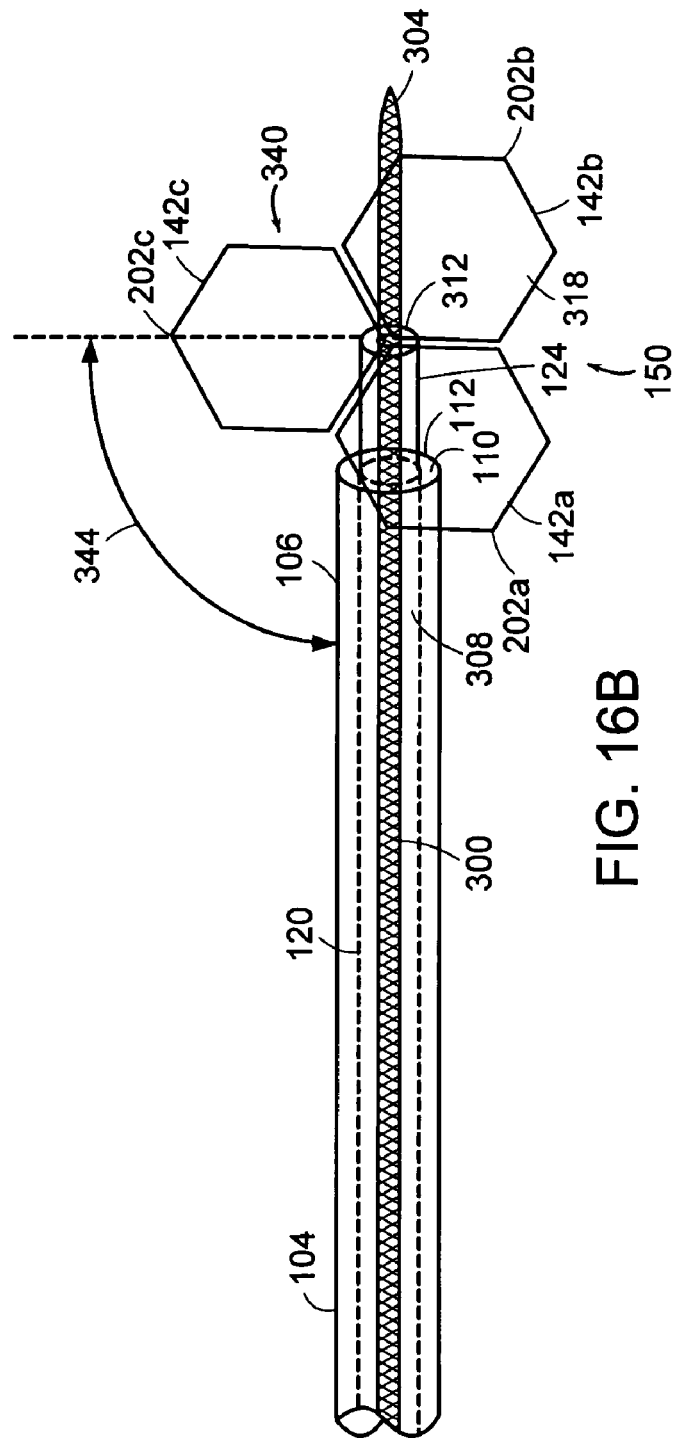
FIG. 16A
FIG. 16B

TRANSSEPTAL PUNCTURE APPARATUS

RELATED APPLICATIONS

This application claims priority to and the benefit of U.S. Ser. No. 60/517,983, filed Nov. 6, 2003, the contents of which are incorporated by reference herein.

FIELD OF THE INVENTION

The invention generally relates to a device for performing an intracardiac transseptal puncture procedure. More specifically, the device relates to transseptal puncture of the atrial septum for the treatment of intracardiac defects such as patent foramen ovale (PFO) and other therapeutic applications for diseases associated with the heart.

BACKGROUND OF THE INVENTION

Septal puncture is utilized in patients in which a communication is present between the two atria of the heart, for example, a patient with a patent foramen ovale n(PFO). A PFO consists of two layers of overlapping but unfused tissues, the septum primum and the septum secundum, forming a tunnel like "hole" between the two tissues that can put the patient at a high risk of embolic stroke. Due to the tunnel-like nature of many PFOs, an occlusion device that is used to repair the PFO often does not sit flat on the septal wall when it is implanted, such that a portion of the occluder is positioned in the PFO tunnel. For this reason a second hole in the septum primum part of the atrial septum near the PFO is introduced by septal puncture through which the occlusion device is then positioned (rather than through the PFO tunnel).

Septal puncture through an intact atrial septum from the right atrium to the left atrium is also often necessary. This is traditionally performed using rigid, long needles, such as Brockenbrough or Ross needles. In all types of septal puncture, the needle that is used to puncture the atrial septum poses a high risk of inadvertent puncture through tissue other than the septum primum, for example, the atrial free wall, posing a significant risk to the patient. For PFO closure, this risk is potentially even higher, due to the fact that the septal tissue is defective and often thinning, and may stretch an even greater amount during the puncture procedure, bringing the tip of the needle dangerously close to the atrial free wall or the left atrial appendage.

A device and method that permits the surgeon to safely puncture both an intact atrial septum and an atrial septum having a PFO is therefore needed.

SUMMARY OF THE INVENTION

The invention relates generally to devices and methods for performing a transseptal puncture procedure that are safe alternatives to those currently being performed.

In one aspect, the invention relates to a device for puncturing the atrial septum of a patient. In one embodiment of the invention, the device includes a first, outer needle with a blunt distal end and a lumen longitudinally disposed therethrough and a second, inner needle axially disposed in the lumen of the outer needle. In an embodiment, the inner needle has a proximal portion, an intermediate portion, and a distal portion, wherein the intermediate portion is more flexible than either the proximal portion or the distal portion of the inner needle.

In an embodiment, the intermediate portion is a segment that is approximately 20 mm from the distal end of the inner needle. The intermediate portion may be, for example, 3 mm in length. In an embodiment, the intermediate portion has a waist. The waist of the intermediate portion is, for example, about 0.2 mm in diameter. In a particular embodiment, the intermediate portion of the inner needle may be made of a polymer.

In another embodiment, the inner needle has a distal portion and a proximal portion, wherein the distal portion is more flexible than the proximal portion. In another embodiment, the inner needle is flexible in both the distal portion and the proximal portion (e.g., has homogeneous flexibility).

As another feature, the distal portion of the inner needle has a distal portion that deviates from the linear path of the inner needle such as, for example, a taper, a bend, a curve, a cork screw or a hook. In a particular embodiment, the tip of the inner needle is turned inward during the delivery procedure to avoid the risk of inadvertant puncture of tissue. In another embodiment, the inner needle contains a portion that has a different thickness or diameter than the rest of the inner needle such as, for example, a tapered portion, whereby the inner needle is tapered from one thickness to another.

In an embodiment, the distal portion of the outer needle is more flexible than the proximal portion of the outer needle.

In still another embodiment, the device includes a outer needle with a blunt distal end and a lumen axially disposed therethrough and a pump for introducing a high pressure jet spray through the lumen of the outer needle.

In a further embodiment of the invention, the device has a outer needle with a blunt distal end and an insulating material for insulating the length of the proximal and intermediate portion, leaving the distal tip of the outer needle uninsulated. As an additional feature, the device may include unipolar electrodes or, alternatively, the device may include bipolar electrodes.

In another aspect, the invention provides a method for puncturing the atrial septum of a patient's heart by accessing the right atrium via a vessel. The method includes introducing into the right atrium a transseptal puncture device that includes a first outer needle with a blunt distal end and a lumen longitudinally disposed therethrough and a second inner needle axially disposed in the lumen of the outer needle, the inner needle having a proximal portion, a distal portion, and an intermediate portion that is more flexible than the proximal portion or the distal portion. The outer needle is contacted with the atrial septum and the inner needle is pushed through the septum in advance of the outer needle. A delivery sheath is then positioned using a standard catheterization laboratory technique in the left atrium and the transseptal puncture device is withdrawn from the patient's body.

In another aspect, the invention provides a method for puncturing the atrial septum of a patient's heart by accessing the right atrium via a vessel. The method includes introducing into the right atrium a transseptal puncture device that includes a first, outer needle with a blunt distal end and a lumen longitudinally disposed therethrough and a second, inner needle axially disposed in the lumen of the outer needle, the inner needle having a proximal portion and a distal portion, wherein the distal portion is more flexible than the proximal portion. The outer needle is first contacted with the atrial septum. The inner needle is then pushed through the septum in advance of the outer needle. A delivery sheath is positioned in the left atrium and the transseptal puncture device is withdrawn from the patient's body.

BRIEF DESCRIPTION OF THE DRAWINGS

In the drawings, like reference numbers generally refer to the same parts throughout the different views. Also, the drawings are not necessarily to scale, emphasis instead generally being placed upon illustrating the principles of the invention.

FIG. 1 is a plan view of a transseptal puncture device according to an illustrative embodiment of the invention.

FIG. 2 is a longitudinal plan view of the distal end of a transseptal puncture device according to an illustrative embodiment of the invention.

FIG. 3 is a cross sectional view of the distal end of a transseptal puncture device taken along lines 3-3 in FIG. 2.

FIG. 14A is a schematic side view of an embodiment of a flexible member according to the invention.

FIG. 14B is a schematic end-on view of the flexible member of FIG. 14A.

FIG. 15A is a schematic side view of an embodiment of a flexible member according to the invention.

FIG. 15B is a schematic end-on view of the flexible member of FIG. 15A.

FIG. 16A is a schematic side view of an embodiment of a set of flexible members, a cutting member, and an elongate member of a portion of a septal puncture apparatus according to the invention.

FIG. 16B is an illustration of the set of flexible members and the cutting member extended out of the elongate member of FIG. 16A.

DETAILED DESCRIPTION OF THE INVENTION

Figure 4A:
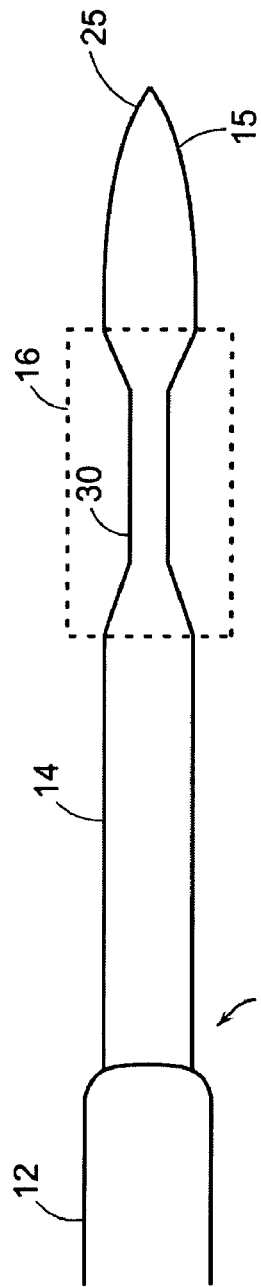
FIG. 4A is a longitudinal view of the distal end of an inner needle of a transseptal puncture device according to an illustrative embodiment of the invention in which the intermediate portion contains a waist.

The invention described herein relates to devices and methods for puncturing the atrial septum via the percutaneous route for the treatment of intracardiac defects such as, for example, patent foramen ovale, intracardiac sources of emboli that may cause embolic stroke, and defects related to cardiac disease.

In one aspect, the invention relates to a percutaneous device for making a transseptal puncture in the atrial septum of the heart. FIG. 1 is a plan view of the transseptal puncture device according to an illustrative embodiment of the invention. The illustrative percutaneous device 10 includes a first, outer needle 12 including a lumen 13 axially disposed along the long axis of the outer needle 12 and including a blunt distal end 17 having an opening 18. A second, inner needle 14 is axially disposed within the lumen of the outer needle 12. The outer needle 12 provides structural support for the inner needle 14 and also functions as a dilator of the hole created in the atrial wall by the inner needle 14. The device 10 may further feature a transcutaneous intravascular sheath 22 through which the device 10 passes from outside the patient's body through a vessel, for example, the femoral vein, through the inferior vena cava to the right atrium, and a control handle 26 at the distal end 27 of the sheath 22. The sheath and/or other components of the delivery system may be steerable by actuators (not shown) on the control handle 26 to aid in delivering the device along the tortuous vascular path leading to the patient's right atrium. In certain embodiments, the distal end 17 of the outer needle 12 is tapered toward the inner needle 14, and the distal end 27 of the sheath 22 is tapered toward the outer needle 12.

In an embodiment, the outer needle 12 is similar in size to a Brockenbrough needle, e.g., with tip diameter of about 0.8 mm. The percutaneous device 10 also features a septal perforator, for example, a second, inner needle 14. Alternatively, the septal perforator is a radio frequency electrode (not shown) that is coupled to the outer needle 12, or is a high pressure jet spray (not shown) that is emitted from the opening 18 of the outer needle 12.

In an embodiment depicted in FIGS. 2 and 3, the inner needle 14 includes a sharp tip 25 at a distal end 15 of the inner needle 14. The inner needle 14 is axially disposed within the lumen 13 of the outer needle 12. The inner needle 14 is reciprocally and axially moveable in the lumen 13 of the outer needle 12. The inner needle 14 can be rotated as well. The distal end 15 of the inner needle 14 is extendable through the opening 18 at the distal end 17 of the outer needle 12. The inner diameter of the lumen 13 of the outer needle 12 typically approximates the outer diameter of the inner needle 14.

The outer needle 12 and the inner needle 14 are made from various metals such as, for example, nitinol, steel, or titanium, or alloys thereof or polymers such as polyimide, PEBAX®, polyethylene, polytetrafluoroethylene (EPTFE), Fluorinated-ethylenepropylene (FEP), and polyurethane. In one embodiment, the inner needle 14 is solid to increase its sharpness. Alternatively the inner needle 14 is hollow. The use of the outer needle 12 for introducing the inner needle 14 into the patient's cardiac tissue is preferred. In another embodiment, a dilator that is made from material that provides sufficient support during the transseptal puncture procedure is used and the outer needle 12 may not be needed.

Figure 4B:
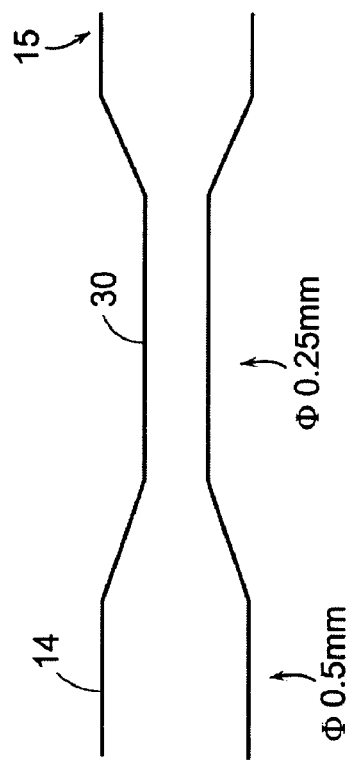
FIG. 4B is an exploded view of the intermediate portion of FIG. 4A.

FIGS. 4A and 4B are a longitudinal view and an exploded view, respectively, of the distal end of an inner needle of a transseptal puncture device according to another illustrative embodiment of the invention. The illustrative inner needle 14 includes a waist 30 near the distal end 15 of the inner needle 14. The waist 30 is positioned on an intermediate portion 16 of the inner needle 14 that is narrower in diameter than the portion of the inner needle 14 that is proximal to the intermediate portion 16 and the portion of the inner needle 14 that is distal to the intermediate portion 16. The waist 30 is thereby more flexible or bendable than the portions of the inner needle 14 that are proximal or distal to the waist 30. In one embodiment, the distal portion 15 is more flexible than the proximal portion 11 of the inner needle 14. The intermediate portion 16 having waist 30 is positioned about 5 mm to about 30 mm, preferably about 20 mm proximal to the distal end 15 of the inner needle 14. In an embodiment, the diameter of the waist 30 ranges from about 0.1 mm to about 0.5 mm, e.g., if the waist is composed of a metal, while the diameter of the inner needle 14 proximal to the waist 30 ranges from about 0.5 mm to about 1.5 mm and the diameter of the inner needle 14 distal to the waist 30 ranges from about 0.2 mm to about 1 mm. In another embodiment, the diameter of the waist 30 ranges from about 0.1 to about 1 mm, e.g., if the waist is composed of a non-metal, such as, for example, a polymer, such as (PEBAX) or polyurethane, a plastic, rubber, or any other polymer deemed suitable to those skilled in the art. In that case, the diameter of the inner needle 14 proximal to the waist 30 ranges from about 0.5 mm to about 3.0 mm and the diameter of the inner needle 14 distal to the waist 30 ranges from about 0.2 mm to about 3.0 mm. For example, the diameter of the waist 30 is about 0.2 mm, the diameter of the inner needle 14 proximal to the waist 30 is about 1 mm and the diameter of the inner needle 14 distal to the waist 30 is about 0.4 mm.

Figure 5:
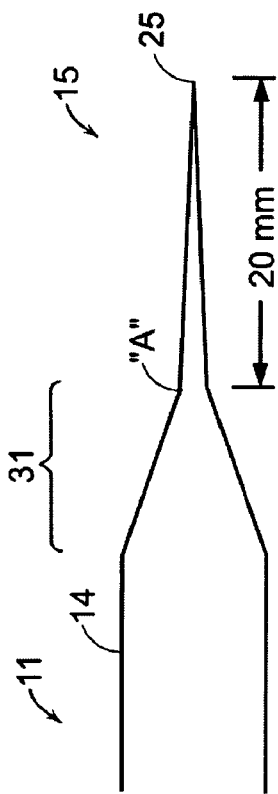
FIG. 5 is a longitudinal view of the distal end of an inner needle of a transseptal puncture device according to another illustrative embodiment of the invention in which the inner needle has a tapered intermediate portion.

FIG. 5 is a longitudinal view of the distal end of an inner needle of a transseptal puncture device according to another illustrative embodiment of the invention. In one embodiment, the inner needle 14 diameter is larger (e.g., 1 mm larger) at the proximal end of the inner needle 14 than the distal end 17. Alternatively, the inner needle 14 diameter is larger throughout the length of the inner needle 14 except for the most distal about 20 mm of the distal end 15. In one embodiment, the inner needle 14 contains a portion 31 at the distal end 15 that is tapered or the diameter of the inner needle 14 is gradually stepped down, for example, to a diameter of about 0.1 to about 0.25 mm, preferably about 0.2 mm, at a point "A" about 10 mm to about 20 mm proximal to the tip 25 of the inner needle 14. In an embodiment, the diameter of the inner needle 14 from the tip 25 to the point "A" is uniform. In a particular embodiment, the distal about 10 mm of the inner needle 14 adjacent to the tip 25 has a diameter of about 0.2 mm. According to this embodiment of the invention, the distal end 15 of the inner needle 14 is thinner and therefore is more flexible than the proximal portion 11 of the inner needle 14. In another embodiment the tapered or step-down portion 31 can extend to the tip 25 of the inner needle 14 and can be about 5 mm to about 30 mm long.

Figure 6:
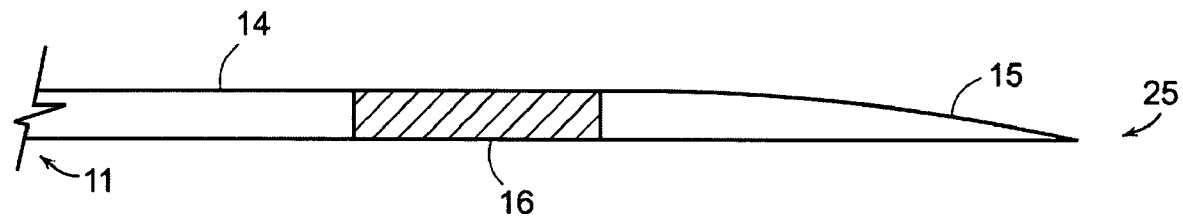
FIG. 6 is a longitudinal view of the distal end of an inner needle of a transseptal puncture device according to another illustrative embodiment of the invention, in which the inner needle has an intermediate portion.

FIG. 6 is a longitudinal view of the distal end of an inner needle of a transseptal puncture device according to another illustrative embodiment of the invention. At a position about 5 mm to about 30 mm, preferably about 20 mm from the distal end 15, the inner needle 14 includes an intermediate portion 16 manufactured from, or coated with, a material or treated such that the intermediate portion 16 is more likely to bend than the portions of the inner needle 14 that are proximal 11 and distal 15 to the intermediate portion 16. For example, if the inner needle 14 is composed of nitinol, the intermediate portion 16 may be annealed at 500 degrees Centigrade for 10 minutes to relieve stress in otherwise superelastic nitinol wire in an as drawn condition. Alternatively, the intermediate portion 16 may be made from a softer material than the proximal portion 11 and distal portion 15 of the inner needle 14. For example, the material of the intermediate portion 16 may be a polymer while the proximal portion 11 and distal portion 15 on the inner needle 14 are made from, for example, a rigid metal or, alternatively, a nickel titanium alloy such as nitinol. The intermediate portion 16 may be welded to, crimped or attached by adhesives to the proximal portion 11 and distal portion 15 of the inner needle 14. In one embodiment, the intermediate portion 16 is about 0.5 mm to about 30 mm, preferably about 2 mm in length. Alternatively, geometric modification may make the intermediate portion 16 more flexible, for example, by the introduction of slits, grooves, cut-aways, notches, dimples, or other modification that thins portions of the wall of the intermediate portion 16.

In another embodiment (not shown), the distal, the proximal, and/or the intermediate portion (if present) of the inner needle 14 is flexible.

Figure 7:
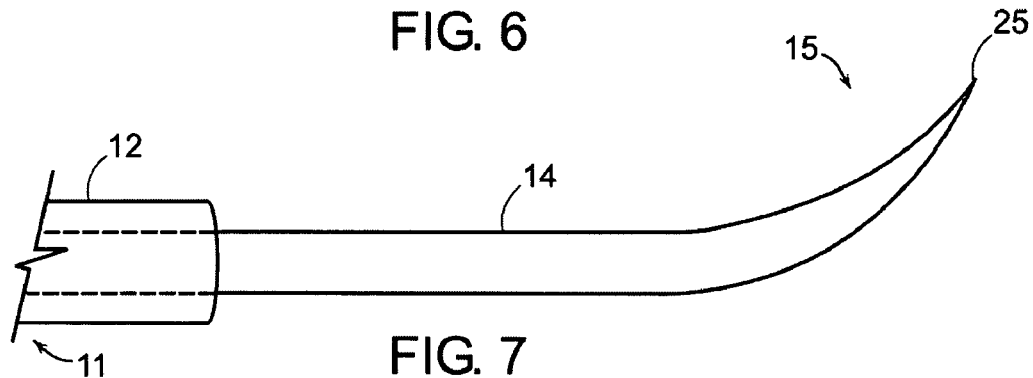
FIG. 7 is a longitudinal view of the distal end of an inner needle of a transseptal puncture device according to another illustrative embodiment of the invention in which the distal tip of the inner needle is bent.

FIG. 7 is a longitudinal view of the distal end of an inner needle of a transseptal puncture device according to another illustrative embodiment of the invention. The distal end 15 of the illustrative inner needle 14 may be straight (e.g., 0 degrees) or is bent at an angle ranging from about >0 degrees to about 270 degrees, preferably about 180 degrees relative to the long axis of the inner needle 14.

Figure 8:
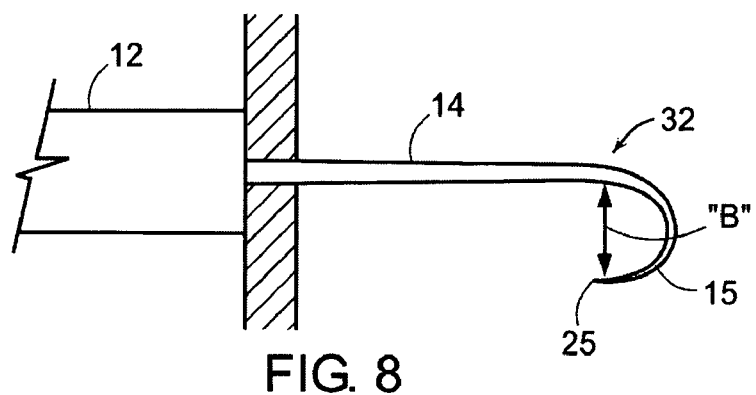
FIG. 8 is a longitudinal view of the distal end of an inner needle of a transseptal puncture device according to another illustrative embodiment of the invention in which the distal end of the inner needle has a hook.

Alternatively, referring to FIG. 8, when the distal end 15 of the inner needle 14 is not constrained within the lumen 13 of the outer needle 12, the distal end 15 has an essentially non-traumatic conformation, such as a helical, curved, cork screw, or hook shape. For example, the diameter "B" of the loop that forms the hook 32 can be between about 5 mm and about 30 mm, preferably about 10 mm. When the distal end 15 is enclosed within the lumen 13 of the outer needle 12, the entire length of the inner needle 14 is substantially straight and parallels the long axis of the outer needle 12.

In an alternative embodiment of the transseptal puncture device, the inner needle is replaced by a pulsating high pressure saline jet (or other suitable fluid) (not shown) generated by a pump. The jet spray is directed to the atrial septum from the distal end of the blunt, outer needle according to the invention and incises the tissue. The outer needle is then gradually advanced through the incision. Because the incision is made gradually and slowly, the method is safer than the currently used methods, for example, because there is a reduced risk of trauma and/or bleeding.

In yet another embodiment of the transseptal puncture device, the blunt, outer needle is replaced by a radio frequency (RF) apparatus (not shown). The outer needle according to the invention is insulated except for the outer needle tip. The alternating current travels down the outer needle. Preferably, unipolar electrodes can be used for the outer needle with grounding pads typically placed on the patient's thighs. Alternatively, a bipolar electrode system can be employed as well. The application of RF to the outer needle increases the tissue temperature around the outer needle tip to over 100 degrees C. Mechanical cohesion in the tissue is diminished and allows the outer needle to be advanced as pressure is applied to the tissue by the outer needle tip. Any other method producing heat (e.g., such as electrical resistance, laser, or ultrasound) can be potentially used instead of RF. As with the saline jet described above, the incision is created slowly therefore the risk of accidental puncture of tissue that is not targeted for incision is minimal.

Figure 9A:
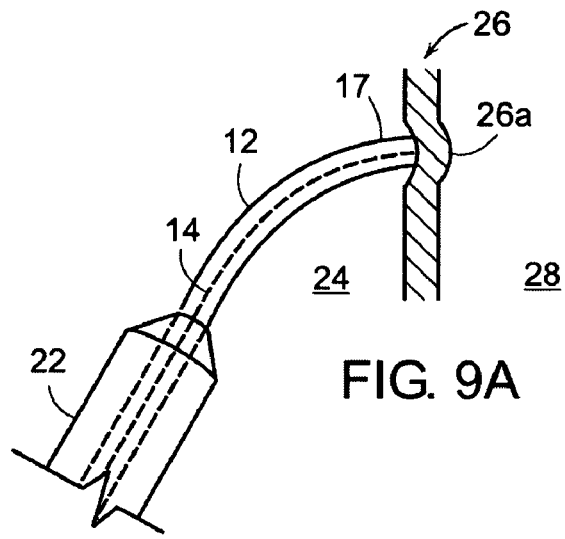
FIGS. 9a-9g depicts the steps in an illustrative method for puncturing an atrial septum with an illustrative transseptal puncture device according to the invention.

In another aspect, the invention provides a method using a percutaneous approach for puncturing the atrial septum of a patient to treat, for example, patent foramen ovale or to gain access to the left atrium to ablate the left atrial appendage. FIGS. 9A-9E depict the steps of an illustrative method for puncturing an atrial septum with the transseptal puncture device according to the invention. The illustrative method includes the step of introducing an intravascular sheath 22 in a vessel to access the lumen of the right atrium 24. In an embodiment, the sheath 22 is tapered to enhance advancement of the sheath 22 though the atrial septum 26. Referring to FIG. 9A, after the sheath 22 is properly positioned in the right atrium 24, the outer needle 12 of the transseptal device 10 is advanced distally toward the atrial septum 26 and positioned against septum primum 26a at the puncture site. The blunt distal end 17 of the outer needle 12 is then pushed against septum primum 26a until some tenting of the atrial septum 26 is visible. The tenting should be sufficient to correctly identify the puncture site in the septum primum 26a. Alternatively, visualization techniques such as, three-dimensional echocardiogram or magnetic resonance imaging can be used that may work without tenting. Some amount of tenting also assists with the puncture itself.

Figure 9B:
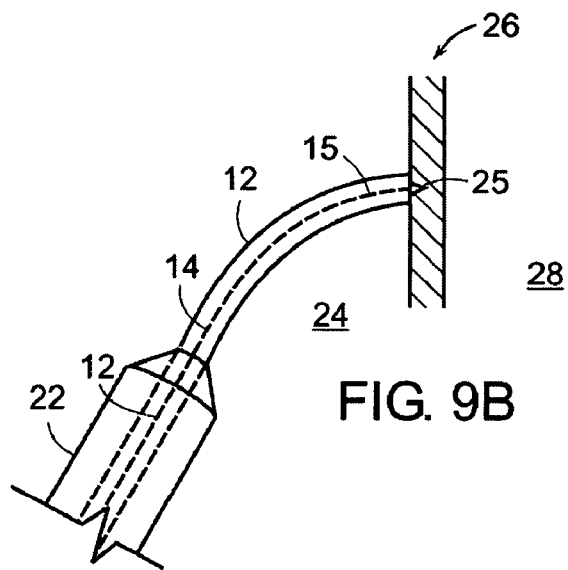

Referring to FIG. 9B, once the outer needle 12 is positioned, the inner needle 14 is advanced relative to the outer needle 12 through the septum 26. At its most distal position, about 10 mm of the inner needle 14 should extend from the distal end 17 of the outer needle 12. Alternatively, the most distal position could be about 30 mm, if the distal portion 15 of the inner needle 14 had a hook shape, as is shown in FIG. 8. In an embodiment, the transition from the hook portion to the straight portion of the inner needle 14 is exposed. The outer needle 12 follows the path of the inner needle 14 through the septum 26. Because of the fine diameter, extreme sharpness, and the added stiffness provided by the outer needle 12, the inner needle 14 can be initially advanced into the septum 26. The motion of the inner needle 14 may be forward, vibrating, reciprocating, linear, or rotational, for example. In one embodiment, movement of the inner needle 14 is accomplished manually. Alternatively, movement of the inner needle 14 may be automated and therefore require additional controls such as a spring-loaded needle to be attached to the delivery system components such as the sheath 22. Such devices of the invention are easier for the doctor to manipulate and safer for the patient.

Figure 9C:
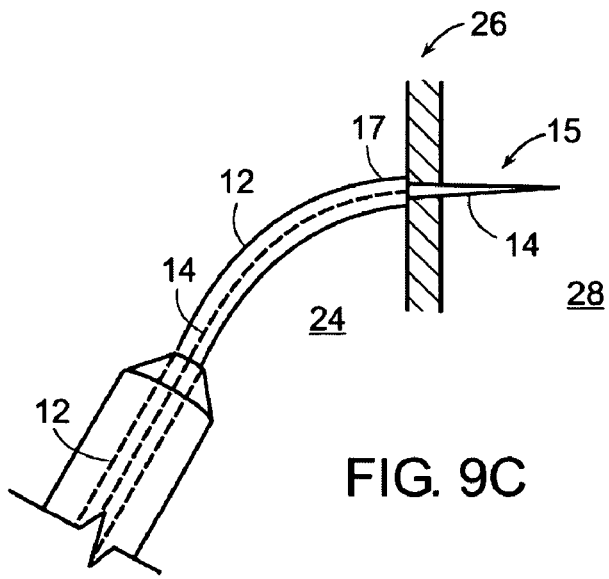
Figure 9D:
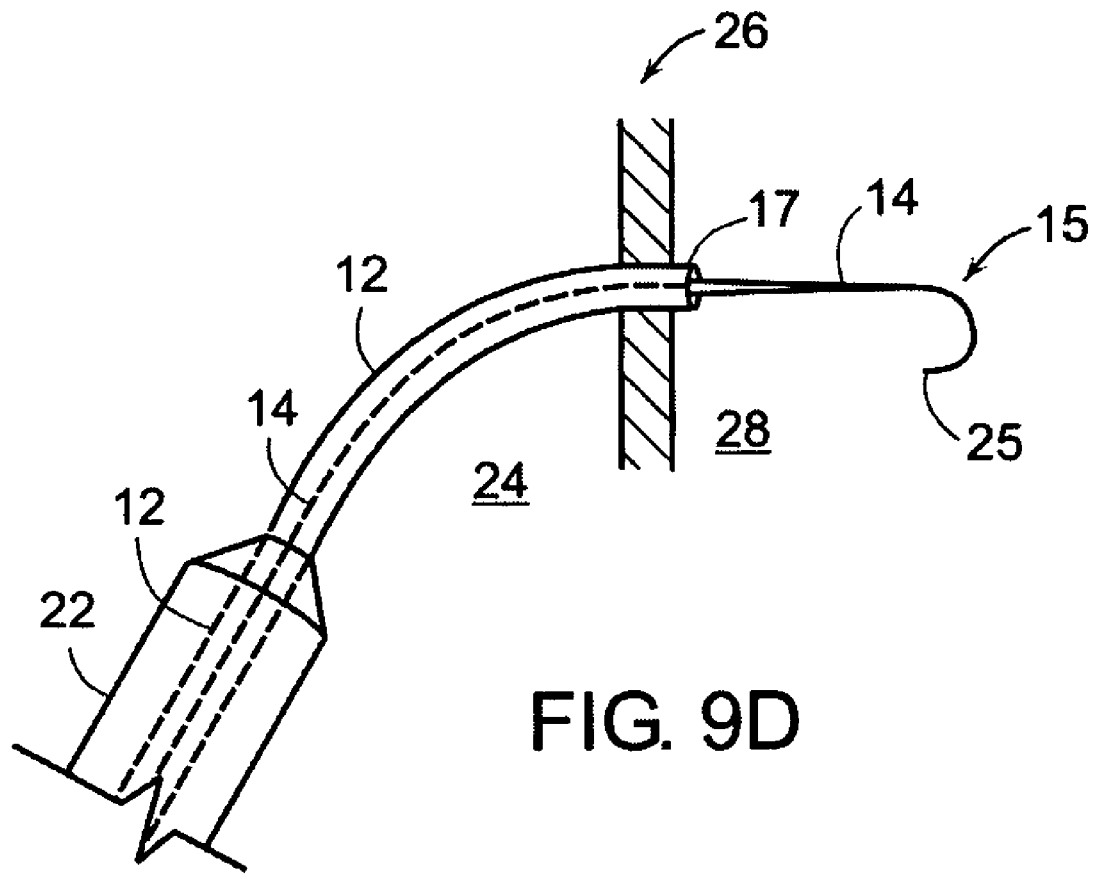
Figure 9E:
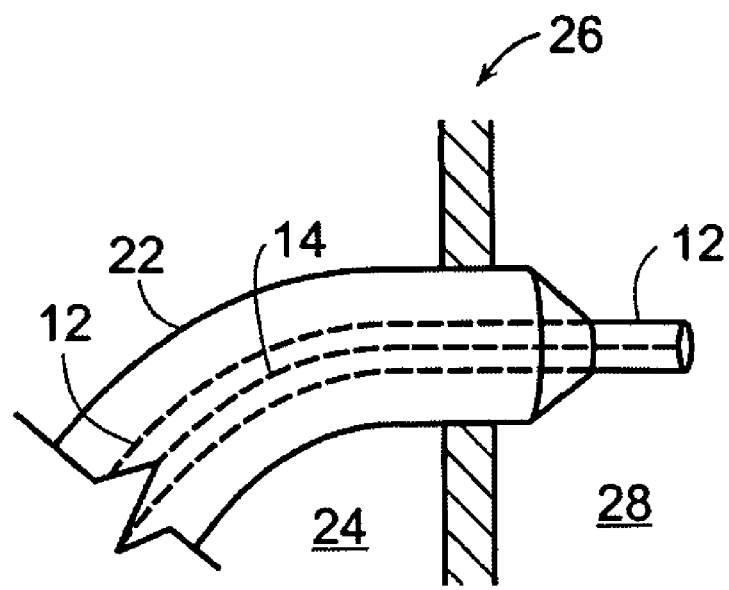
Figure 9F:
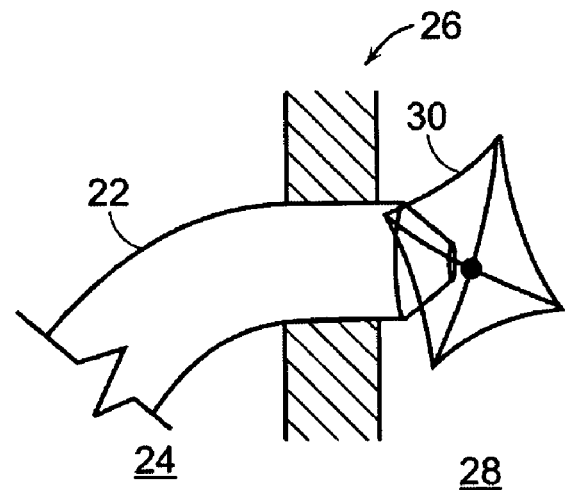
Figure 9G:
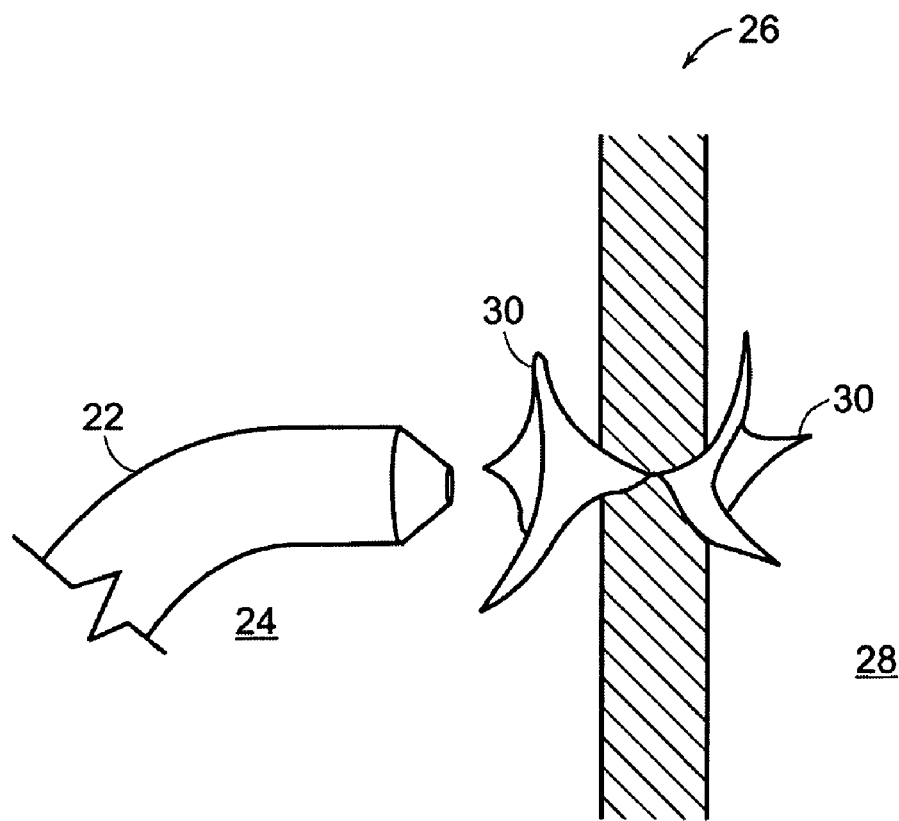

Referring now to FIG. 9C, once the distal end 15 of the inner needle 14 is positioned within the septum 26, the tissue provides support to the exposed part of the inner needle 14 until the whole tip of the inner needle 14 is delivered into the left atrium 28. Referring to FIG. 9D, the outer needle 12 is advanced and positioned in the left atrium 28. Referring to FIG. 9E, standard catheterization laboratory procedures are utilized to place the sheath 22 within the left atrium 28. Once the sheath 22 is in the left atrium 28, the other components of the device, for example, the inner needle 14 and the outer needle 12, can be completely removed from the sheath 22 and the sheath 22 can be used to deliver implants, for example, such as an atrial occluder for the treatment of a patent foramen ovale, sutures, or other intracardiac therapeutic devices. For example, referring to FIG. 9F, one half of an occluder 30 is released from the sheath 22 and positioned in the left atrium 28. Referring to FIG. 9G, the sheath 22 is then withdrawn into the right atrium 24 and the other half of the occluder 30 is released and positioned in the right atrium 24. In an embodiment, the inner needle 14 is left behind, traversing the puncture site, and acts to maintain the puncture site as well as to act as a guidewire (e.g., and the other outer needle 12 is withdrawn). In another embodiment, the inner needle 14 is withdrawn, e.g., into the outer needle 12.

The method for transseptal puncture using the transseptal device described herein is advantageous over conventional methods. For example, when using the devices and methods of the invention inadvertent contact of the inner needle 14 with the left atrial free wall (not shown) immediately after the septum 26 is punctured does not result in damage to or perforation of the left atrial free wall because the distal end 15 of the inner needle 14 is very flexible, as illustrated, for example, in FIG. 4 and corresponding text, or has an alternative tip 25, as illustrated, for example, in FIG. 8 and corresponding text, when fully extended from the distal opening 18 of the outer needle 12. When the distal end 15 of the inner needle 14 contacts the left atrial free wall, the distal end 15 of the inner needle 14 harmlessly bends rather than perforates the left atrial free wall. In one embodiment, the distal end 15 of the inner needle 14 bends because of the enhanced flexibility of the inner needle 14 at the intermediate portion 16, as described above in connection with FIGS. 4-8, between the proximal portion 11 and distal portion 15 of the inner needle 14. In an embodiment, perforation of the left atrial wall is avoided by modifying the shape of the inner needle 14 to form, for example, a hook or a bend.

Another advantage of the transseptal puncture devices described herein is the ability of the device to puncture through thick septum such as septum secundum. The transseptal puncture devices according to the invention can be used for remote suturing of a PFO or other defects that may be accessed percutaneously.

The transseptal puncture device according to the invention can also be used with various atrial septal defect locators such as those described in U.S. Ser. No. 10/660,444. For example, the locator may stabilize (e.g., constrain) the motion of the septa during insertion of the inner needle. Generally, a locator system includes a plurality of flexible members, at least one flexible member positionable on a side of the tissue opposite to another flexible member.

Figure 10:
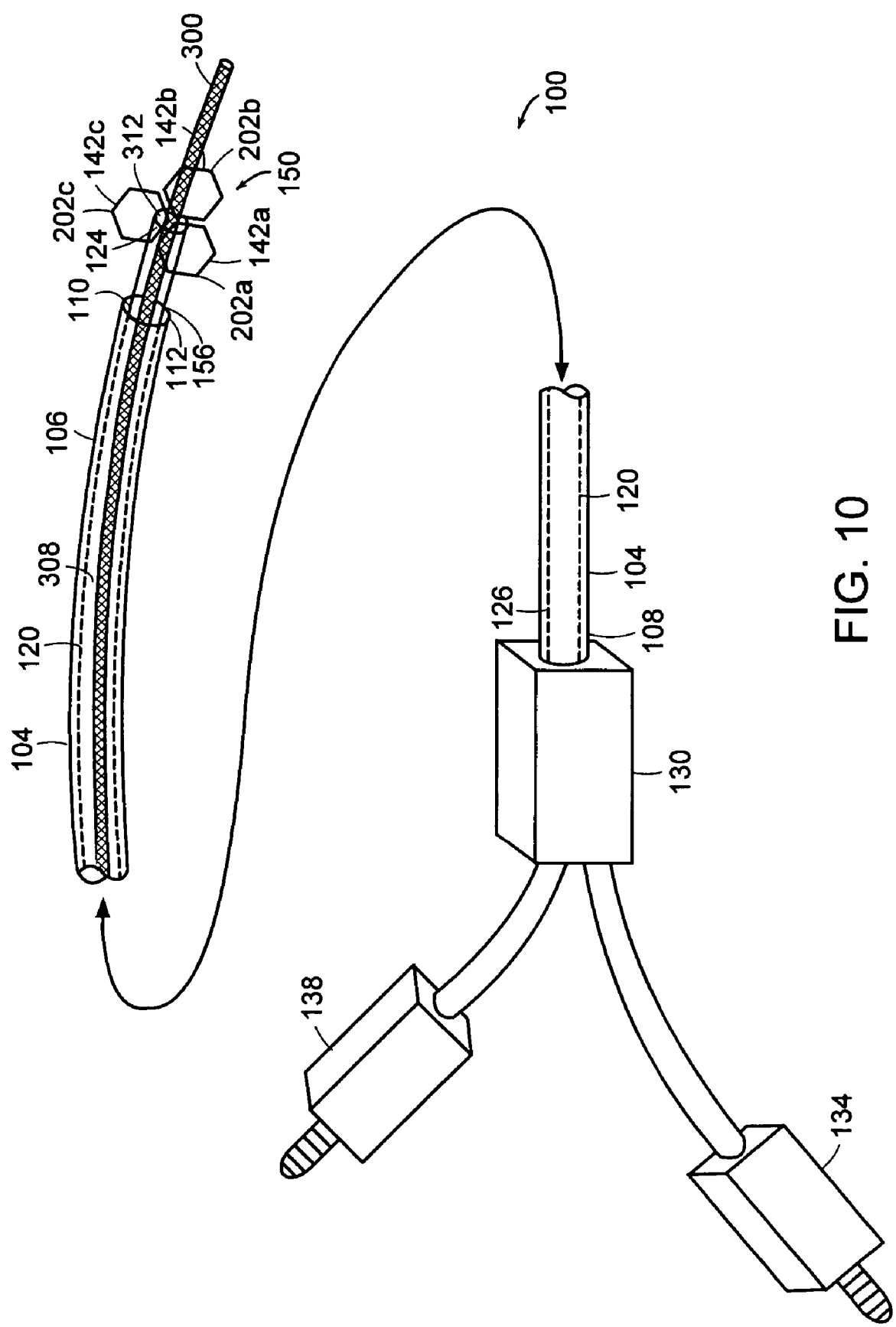
FIG. 10 is a fragmented illustration of a septal puncture apparatus according to an illustrative embodiment of the invention.

FIG. 10 illustrates a septal puncture apparatus 100 including three flexible members 142a, 142b, and 142c (generally 142) coupled to a delivery member 120 for applying, e.g., a pressure or force to a region in a body by pushing, pulling, or restraining the tissue, thereby stabilizing the tissue. The flexible members 142a, 142b, and 142c may be hexagonal in shape and coupled to a distal end 124 of the delivery member 120, thereby forming, generally, a planar array 150. The delivery member 120 is slideably receivable within a lumen 110 of the elongate member 104. Instruments, e.g., the delivery member 120 and a cutting member 300 (e.g., a member that perforate the tissue, which can comprise, referring to FIG. 1, an inner needle 14 and/or an outer needle 12, for example), are slideably receivable in the lumen 110 of the elongate member 104. In this embodiment, the cutting member 300 is slideably receivable in a lumen 308 of the delivery member 120 and extends distally or withdraws proximally from an opening 312 at the distal end 124 of the delivery member 120.

FIG. 10 also illustrates an exemplary interface 130 that permits controllers, for example, a set of apparatus controllers 134 and 138 to communicate with the elongate member 104 and the delivery member 120, respectively. The exemplary controllers 134 and 138 extend, retract, or otherwise manipulate, e.g., the elongate member 104 and the delivery member 120, respectively. A single controller, could, alternatively, control all functions and operations of the tissue puncture apparatus 100 and the instruments disposed therein.

By way of example, the elongate member 104 and the delivery member 120 are flexible tubes fabricated from a biocompatible material, e.g., polyethylene, polyether-amide block co-polymer (PEBAX™), polyurethane, or fluorinated ethylene propylene.

By way of example, the flexible members 142 are manufactured using nickel-titanium material, such as Nitinol™ (Nitinol Devices and Components, Freemont, Calif.), or other shape memory alloy materials. The nickel-titanium wire, when properly manufactured, exhibits elastic properties for the wire to be manipulated (e.g., bent) by an operator and then returned to, substantially, the same shape the wire possessed prior to it being manipulated.

Figure 11:
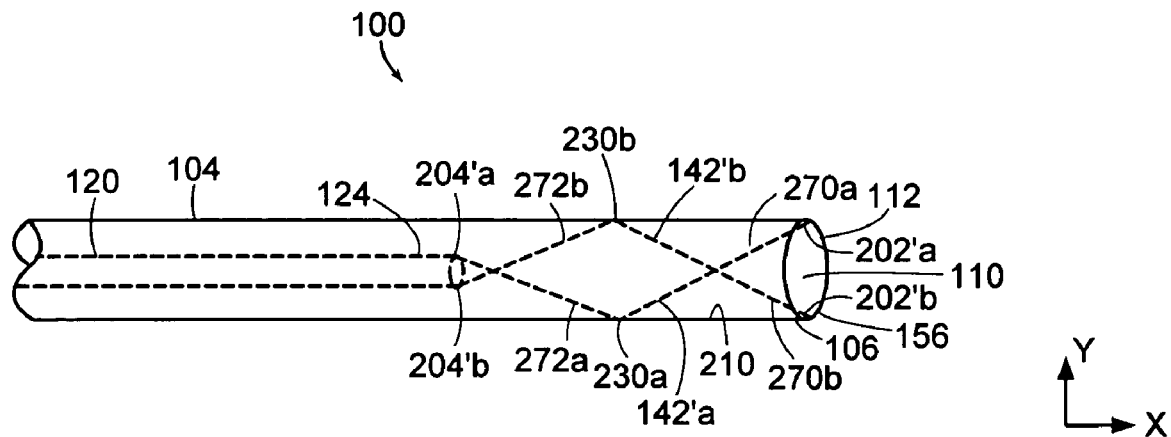
FIG. 11 is a schematic side view of a portion of a septal puncture apparatus including a set of flexible members according to an illustrative embodiment of the invention.

Alternatively, FIG. 11 illustrates a portion of a septal puncture apparatus 100 including exemplary flexible members 142'a and 142'b, which each include a leg such as a wire having a first end 204'a and 204'b, respectively, joined to the distal end 124 of the delivery member 120. Each of the flexible members 142'a and 142'b also have a second distal end 202'a and 202'b, respectively, that is free, i.e., not joined to any other structure of the septal puncture apparatus 100. The longitudinal axis of the flexible members 142'a and 142'b are oriented substantially parallel to the elongate member 104 when the flexible members 142'a and 142'b are located within the lumen 110 of the elongate member 104. The flexible members 142'a and 142'b have a first portion 272a and 272b, respectively and a second portion 270a and 270b, respectively. The flexible members 142'a and 142'b are disposed within the lumen 110 in a contracted position such that the second ends 202'a and 202'b are directed distally towards the opening 112 in the distal end 106 of the elongate member 104. The flexible members 142'a and 142'b are freed from the confines of the lumen 110 by moving the flexible members 142'a and 142'b between the contracted position illustrated, for example, in FIG. 11 and an extended position, such as the extended position depicted in FIG. 12B. After insertion into the lumen 110 of the elongate member 104, the flexible members 142'a and 142'b apply a force to an inner surface 210 of the elongate member 104 in a first location 230a and 230b, respectively, on the inner surface 210 of the lumen 110 that the flexible members 142'a and 142'b contact.

Figure 12A:
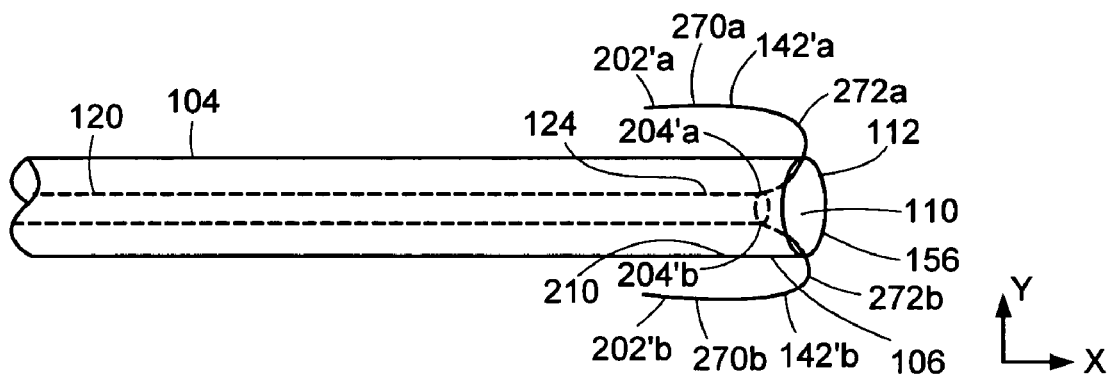
FIG. 12A is a schematic side view of a portion of an embodiment of a septal puncture apparatus including a set of flexible members partially extended from an elongate member.
Figure 12B:
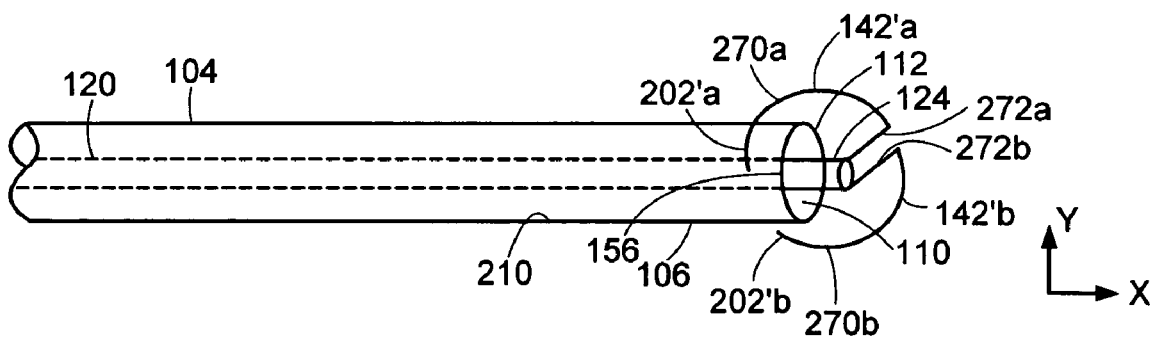
FIG. 12B is a schematic side view of the flexible members of FIG. 12A fully extended from the opening in the elongate member.

Referring now to FIG. 12A, as the delivery member 120 is extended out of the opening 112 of the elongate member 104, the second ends 202'a and 202'b of the flexible members 142'a and 142'b, respectively, undergo an articulation and point, generally, in a proximal direction toward the handle (not shown). Referring now to FIG. 12B, the elongated delivery member 120 is further extended distally along the lengthwise dimension (in the positive direction along the X-axis) of the lumen 110 until the distal end 124 of the delivery member 120 emerges from the opening 112 of the elongate member 104. The second ends 202'a and 202'b of the exemplary preshaped flexible members 142'a and 142'b, respectively, undergo an additional articulation and as a result point, generally, towards one another. In this extended position, each of the flexible members 142'a and 142'b is substantially planar in shape.

Alternatively, the second ends, for example, the second ends 202'a and 202'b, may have a different diameter than other locations along the length of the flexible elastic members 142'a and 142'b. By way of example, an operator may select an apparatus having flexible members that have second ends 202'a and 202'b having a larger diameter to, for example, reduce trauma to tissue the second ends 202'a and 202'b contact during use. Alternatively, the second ends 202'a and 202'b may have a ball shaped tip.

Figure 13:
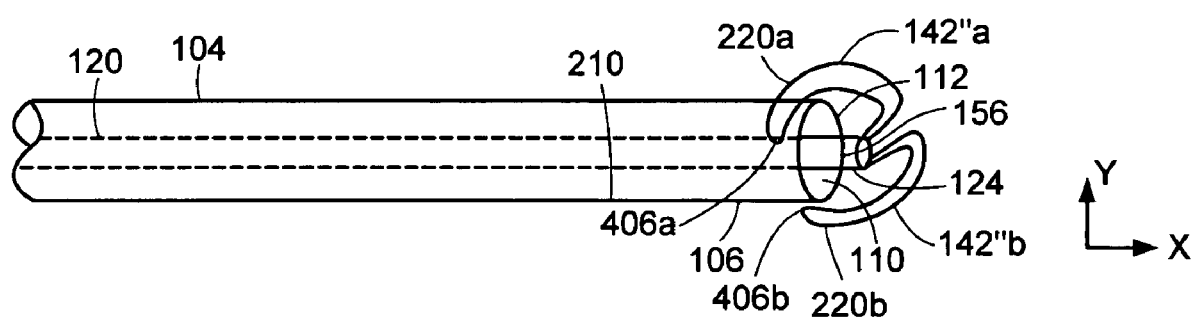
FIG. 13 is a schematic side view of another embodiment of a set of flexible members according to the invention.

FIG. 13 depicts exemplary flexible members 142"a and 142"b that include a first wire loop section 220a and a second loop section 220b, respectively. The tip 406a and 406b of the loop sections 220a and 220b, respectively, point, generally, towards one another and towards the delivery member 120. Loop sections 220a and 220b may, alternatively, be oriented in a variety of directions (e.g., away from the delivery member 120 or at a 45 degree angle away from the delivery member 120).

Referring now to FIGS. 14A and 14B, a septal puncture apparatus 100 includes a single flexible member 142''' that has a middle section 540 located, generally, intermediate the first end 206 and the second end 208 of the flexible member 142'''. The flexible member 142''' thereby forms a closed loop. In this embodiment, the flexible member 142''' is configured so the middle section 540 is located, generally in the center of a plane defined by the flexible member 142''' as illustrated by the end-on view of FIG. 14B. In this configuration, the middle section 540 of the flexible member 142''' aids with stiffening the flexible member 142''', which minimizes bending when, for example, the flexible member 142''' is used by an operator to apply forces to a tissue, e.g., the atrial septum. In this configuration, the flexible member 142 forms a closed loop that is sized and shaped, for example, to contact a first and second side of a tissue.

Referring now to FIGS. 15A and 15B, the flexible elastic member 142'''' is a coil and has a spiral shape. By way of example, in use, a portion 1410 of the flexible member 142'''' can be located on a first side of a tissue and a portion 1420 of the flexible member 142'''' can be located on a second side of a tissue. For example, the flexible member 142'''' can be screwed through a tunnel or a hole, such as a defect in the atrial septum. Alternatively, the distal end 124 of the delivery member 120 may be located axially through, for example, a hole in a tissue such that the flexible member 142'''' may be withdrawn partially through the hole by a rotational (screwlike) motion of the delivery member 120 thereby locating the portion 1410 of the flexible member 142'''' on a first side of the tissue and the portion 1420 of the flexible member 142'''' on a second side of a tissue.

Referring to FIG. 16A, the delivery member 120 is translated axially along the lengthwise dimension of the lumen 110 until the distal end 124 of the delivery member 120 emerges from an opening 112 in the elongate member 104 and the flexible members 142a, 142b, and 142c transition from the contracted first position 330 shown in FIG. 16A to a second extended position 340 shown in FIG. 16B. The exemplary flexible members 142*a*, 142*b*, and 142*c* expand to assume, for example, substantially hexagonal shapes upon emerging from the opening 112 in the elongate member 104 and expanding. The extended flexible members142*a*, 142*b*, and 142*c* are substantially planar. The plane defines a plurality of axes that lie in the plane and the plurality of axes are non-parallel to (i.e., biased relative to) the elongate member 104. An angle 344 defined by at least one of the plurality of axes of the plane of the flexible members 142*a*, 142*b*, and 142*c* and the longitudinal axis of the elongate member 104 is typically specified (e.g., by an operator) such that the flexible members 142*a*, 142*b*, and 142*c* are flush with tissue surface and are capable of applying a force across a large tissue area. For example, the angle 344 might be chosen to ensure the flexible members 142*a*, 142*b*, and 142*c* conform to the shape of a tissue surface abutting the flexible members 142*a*, 142*b*, and 142*c*. If the force is applied, e.g., across a large tissue area the movement of the tissue in any location across the tissue area will be minimized. The flexible members 142*a*, 142*b*, and 142*c* could, alternatively, be of any shape (e.g., polygonal, circular, or ellipsoidal) or of any quantity (e.g., one, two, or five) where the shape and/or quantity of the flexible members 142*a*, 142*b*, and 142*c* are typically selected to distribute as much force as possible while still being able to fit within the lumen 110 of the elongate member 104 and emerge from or retract into the lumen 110.

When the flexible members 142*a*, 142*b*, 142*c* are extended in the second expanded position 340 upon emerging from the opening 112, the exemplary cutting member 300 extends axially in the lumen 308 of the delivery member 120 until a cutting tip 304 of the cutting member 300 emerges from the opening 312 in the distal end 124 of the delivery member 120. The tip 304 of the cutting member 300 cuts the tissue in close proximity to the opening 312 of the delivery member 120.

Figure 17:
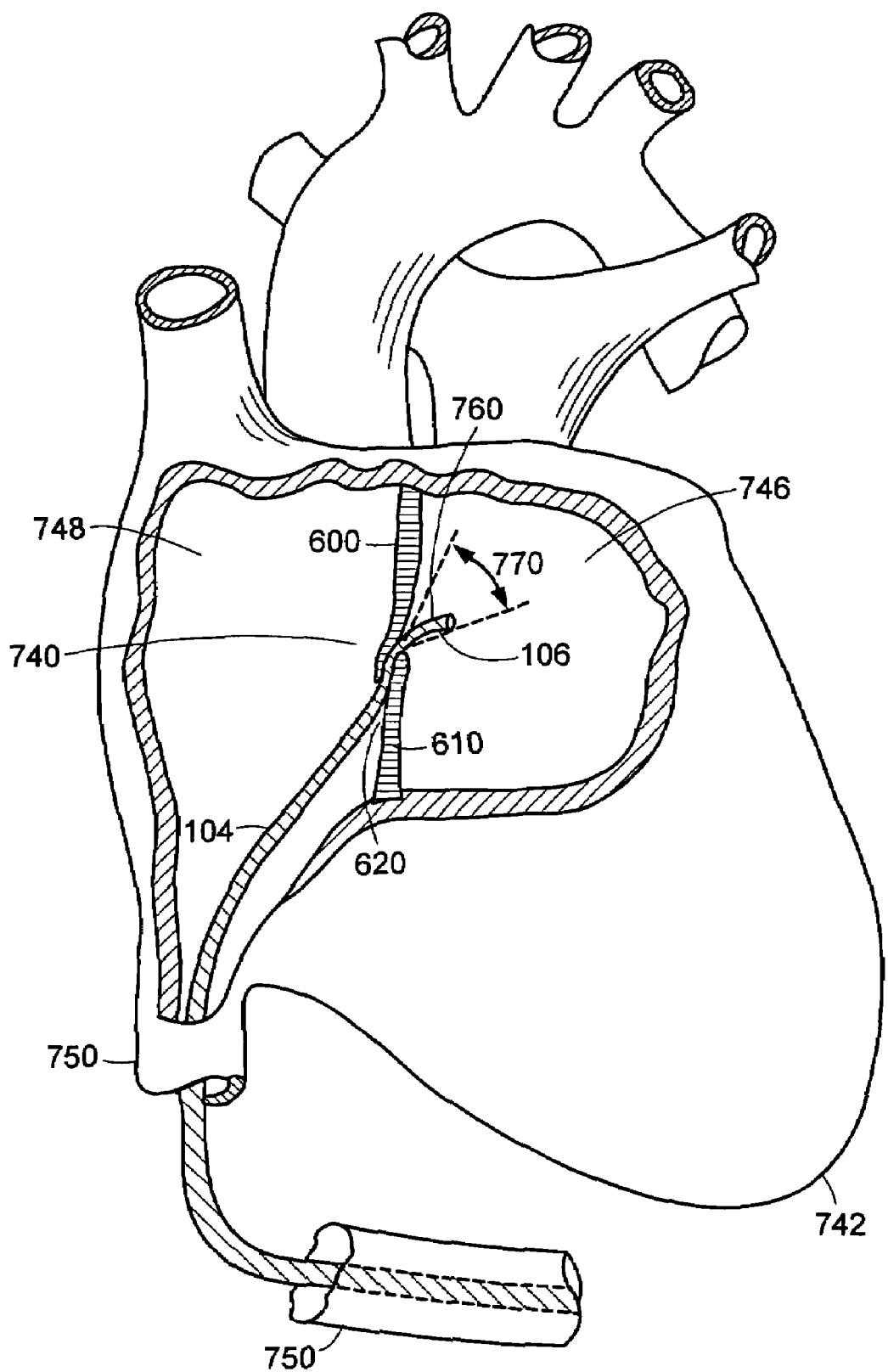
FIG. 17 is a partially broken-away view of a heart depicting a portion of a septal puncture apparatus, according to the invention, on a second side of the septal wall.

Referring now to FIG. 17, an operator introduces an elongate member 104 into the right atrium 748 of a heart 742 through the descending vena cava 750. The elongate member 104 is advanced distally until the distal end 106 of the elongate member 104 passes through a defect 620 (for example, a patent foramen ovale) in the septum 740. The distal end 106 of the elongate member 104 is shown at an angle 770 of about 45 degrees relative to the longitudinal axis of the elongate member 104 due to a bend 760 in the distal end of 106 of the elongate member 104. The bend 760 in the elongate member 104 may be mechanically pre-formed or pre-bent at the angle 770 between about 0 degrees and about 180 degrees prior to insertion of the elongate member into the body. The bend 760 could, alternatively, be accomplished by heating a nickel-titanium material or other shape memory alloy located within the distal end 106 of the elongate member 104.

Figure 18A:
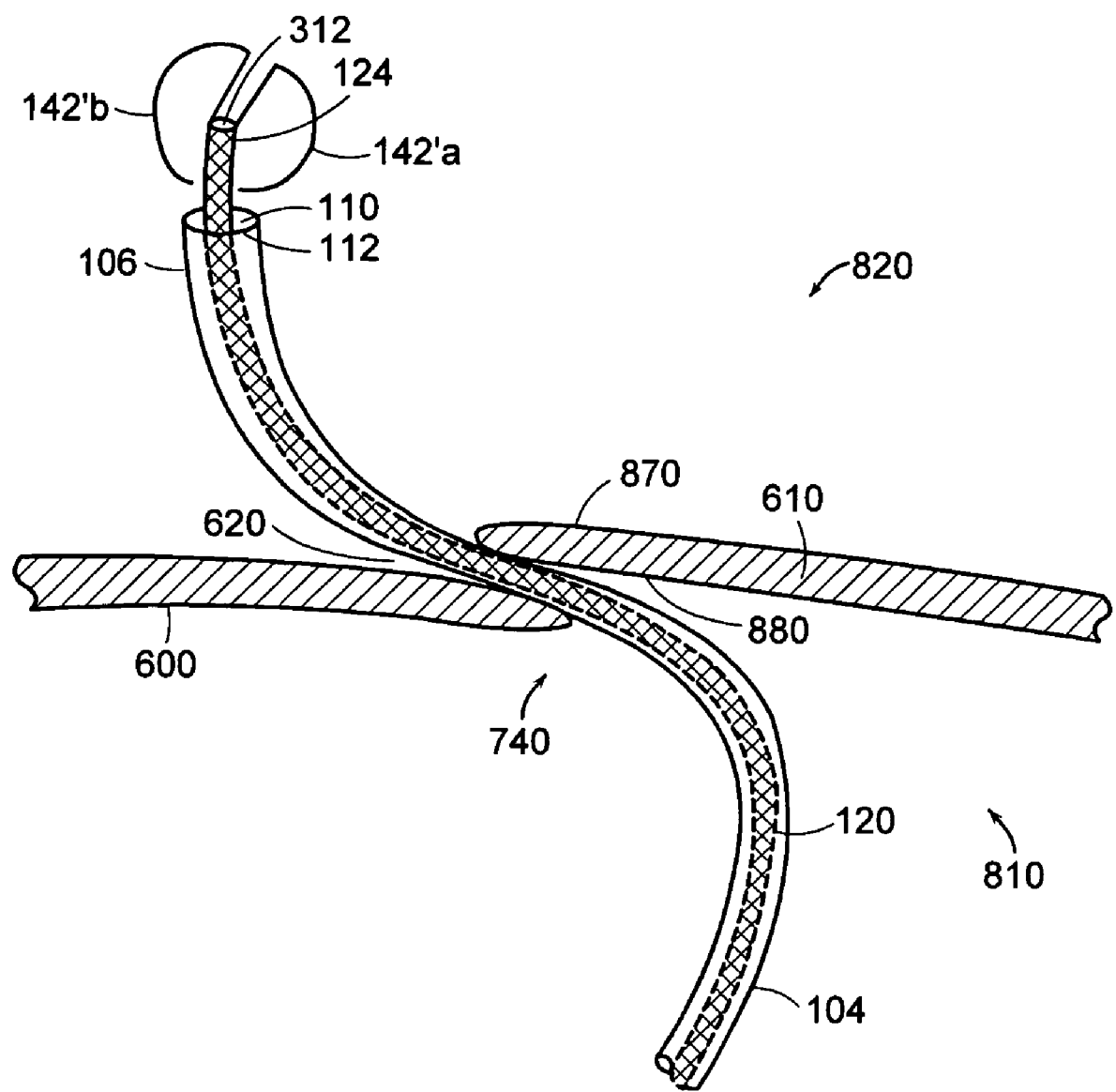
FIG. 18A is a cross-sectional view of a septal wall of a heart depicting a set of flexible members located outside an opening in an end of an elongate member, according to an illustrative embodiment of the invention.
Figure 18B:
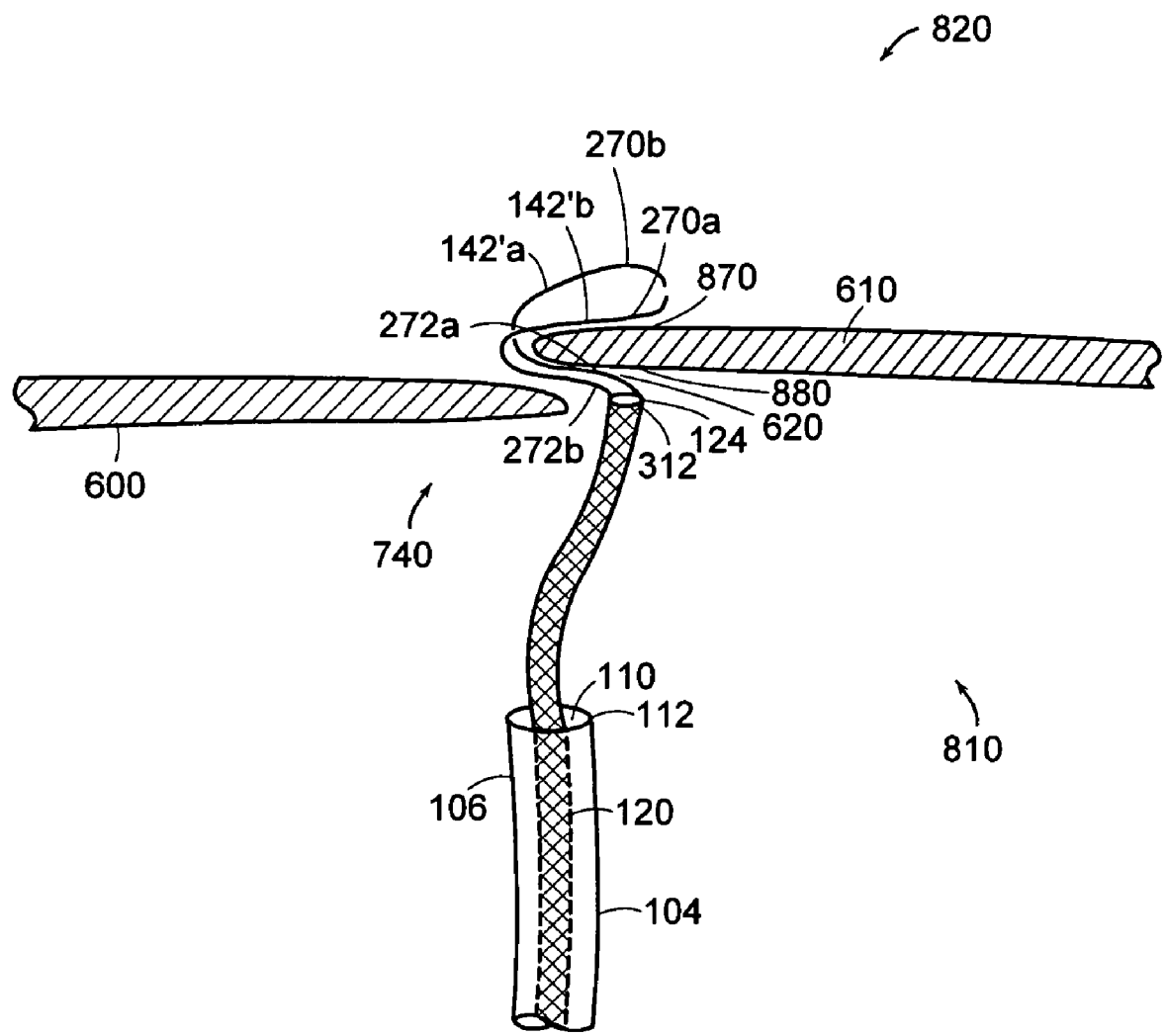
FIG. 18B is a cross-sectional view of the flexible members of FIG. 19A in which a portion of the flexible members is located in contact with a first side of a septal wall and another portion of the flexible members is located in proximity to a second side of the septal wall.
Figure 18C:
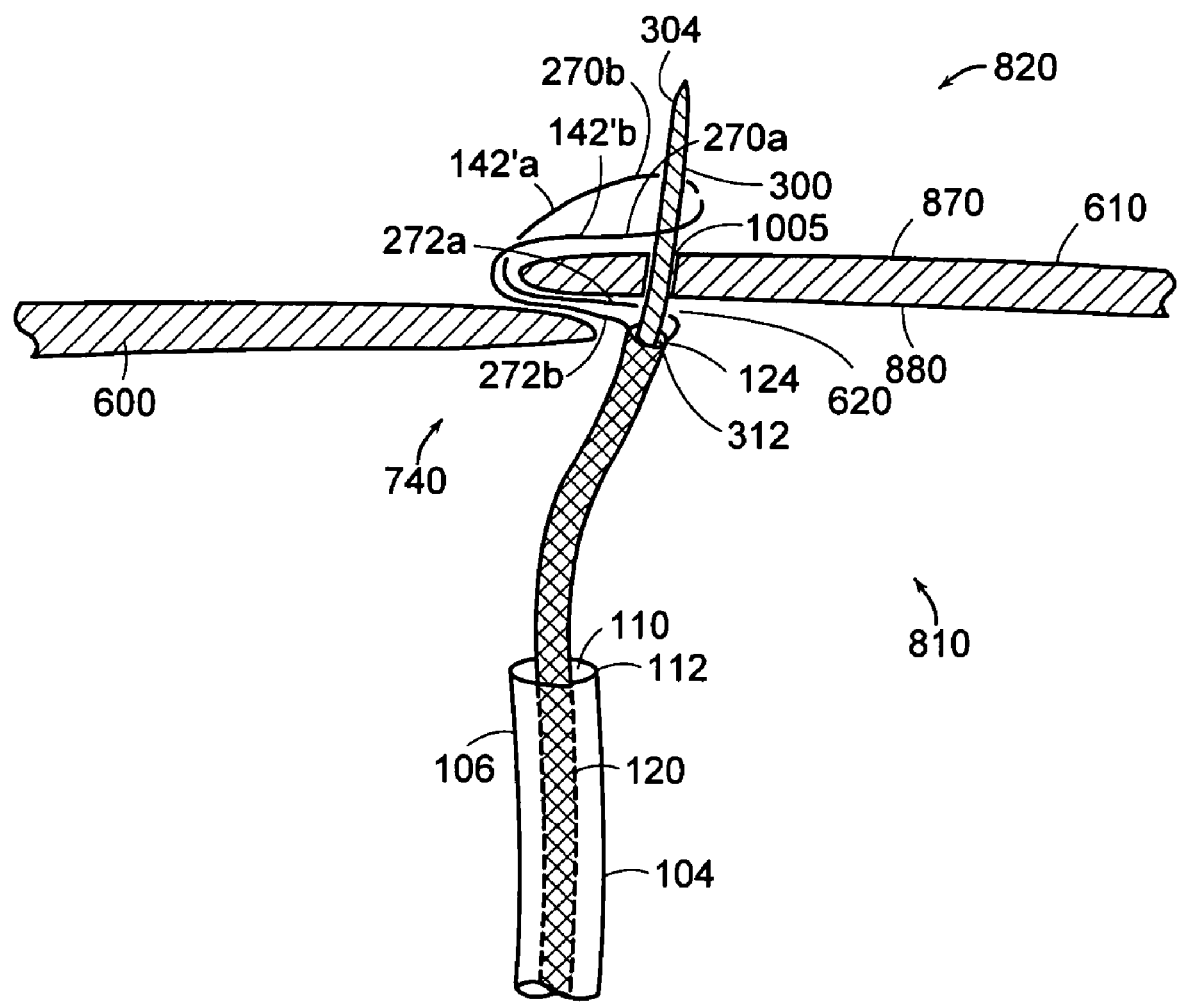
FIG. 18C is a cross-sectional view of the flexible members of FIGS. 19A and 19B in which a cutting member is extended from a lumen in the delivery member creating a hole through the septal wall.

The septal puncture apparatus shown in FIGS. 18A, 18B, and 18C includes two flexible members 142′*a* and 142′*b* coupled to the distal end 124 of the delivery member 120. The flexible members 142′*a* and 142′*b* are initially located within the lumen 110 of the elongate member 104. An operator initially guides the distal end of 106 of the elongate member 104 through the defect (hole) 620 such that the distal end 106 is located on a second side 820 (in the left atria of the heart) of the septum secundum 600 and septum primum 610. Now referring to FIG. 18A, the operator then extends the flexible members 142′*a* and 142′*b* as described herein with respect to, for example, FIGS. 12A and 12B.

With continued reference to FIG. 18A, the elongate member 104 is retracted proximally until the distal end 106 of the elongate member 104 passes back through the defect 620 and is positioned on the first side 810 of the septum 740.

The delivery member 120 is then retracted proximally so the second portions 270*a* and 270*b* of the flexible members 142′*a* and 142′*b* and the distal end 124 of the delivery member 120 are in close proximity to the defect 620, the septum primum 610, and the septum secundum 600 on the second side 820 of the septum 740.

Now referring to FIG. 18B, as the delivery member 120 is further retracted proximally such that the distal end 124 of the delivery member 120 is withdrawn through the defect 620 until it is in contact with or in close proximity to the first surface 880 of the septum primum 610 on the first side 810 of the septum primum 610. The second portions 270*a* and 270*b* of the flexible members 142′*a* and 142′*b* are positioned, generally non-parallel to the longitudinal axis of the elongate member 104 and are in physical contact with at least the second surface 870 of the septum primum 610 on the second side 820 of the septum primum 610 and also partially located within the defect 620 in the septum 740. The first portions 272*a* and 272*b* of the flexible members 142′*a* and 142′*b* are located on the first side 810 of the septum 740. Accordingly, the flexible members 142′*a* and 142′*b* are sized and shaped for contact with the first side 810 and the second side 820 of the septum 740. The flexible members 142′*a* and 142′*b* are thus capable of limiting movement of the septum primum 610. Now referring to FIG. 18C, the cutting member 300 is extended from the opening 312 in the distal end 124 of the delivery member 120. The cutting tip 304 of the cutting member 300 introduces a hole 1005 (tissue opening) through the septum primum 610.

Figure 19:
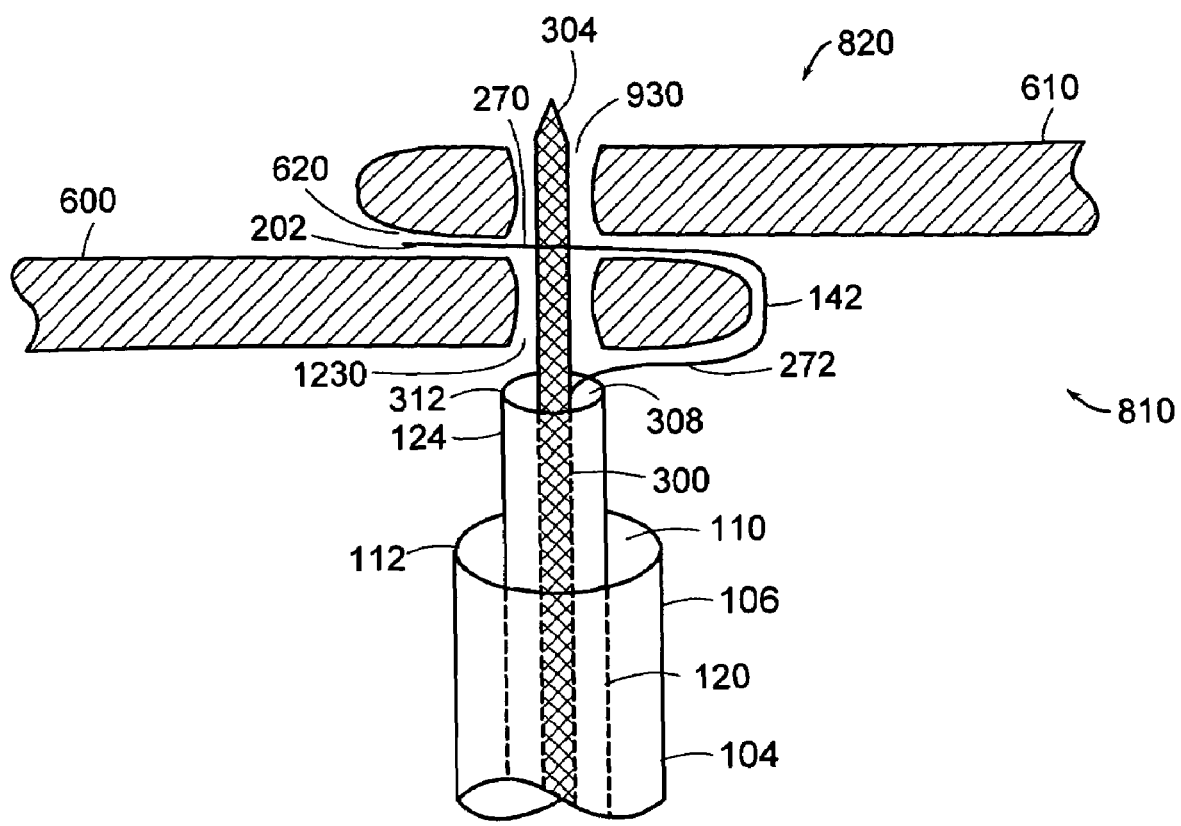
FIG. 19 is a schematic side view of a flexible member, a cutting member, and an elongate member according to an illustrative embodiment of the invention.

Referring now to FIG. 19, an exemplary flexible member 142 is attached to the distal end 124 of the delivery member 120, which extends from the opening 112 in the distal end 106 of the elongate member 104. The delivery member 120 and the elongate member 142 are located on the first side 810 of the septum secundum 600. The distal end 124 of the delivery member 120 is located in close proximity to the tissue surface of the septum secundum 600 on the first side 810 of the septum secundum 600. The flexible member 142 extends through the hole 620 between the septum primum 610 and the septum secundum 600 from the first side 810 to the second side 820. The first side 810 of the septum primum 610 opposes the second side 820 of the septum primum 610. The flexible member 142 is positioned so that the second end 202 and second portion 270 of the flexible member 142 are located on the second side 820 of the septum secundum 600 and the first portion 272 of the flexible member 142 is located on the first side 810 of the septum secundum 600. In this configuration, the flexible member 142 is thus capable of limiting movement of the septum secundum 600. In this embodiment only the septum secundum 600 is secured to limit movement. In alternative embodiments, however, the septum secundum 600 and/or the septum primum 610 may be secured to limit movement.

Additionally, it should be noted that Applicants intend any operable embodiments existing between the devices, methods and applications thereof disclosed in the illustrative embodiments described above to be considered within the scope of the inventions disclosed herein and, as such, claimable subject matter.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

Incorporation by Reference

All publications and patent documents cited in this application are incorporated by reference in their entirety for all purposes to the same extent as if the contents of each individual publication or patent document was incorporated herein.

What is claimed is:

1. A method for treating a patent foramen ovale of a patient's heart, comprising:
    accessing the right atrium via a vessel;
    introducing into the right atrium via said vessel a transseptal puncture device comprising:
        a sheath including a distal end and a longitudinally lumen disposed within;
        an outer needle comprising a blunt distal end and a lumen longitudinally disposed substantially therethrough; and
        a solid inner needle axially disposed in the lumen of the outer needle and moveable beyond the distal end of the outer needle, the solid inner needle comprised substantially of a single material and comprising a proximal portion, an intermediate portion, and a distal portion, wherein the intermediate portion is more flexible than the distal portion and the distal portion is more flexible than the proximal portion, and wherein the distal portion includes a sharp tip configured to pierce the atrial septum;
    contacting the outer needle with the atrial septum adjacent a patent foramen ovale;
    while maintaining contact of the outer needle against the atrial septum, advancing the sharp tip of the solid inner needle through the atrial septum and into the left atrium;
    advancing at least part of the solid inner needle into the left atrium, such that at least one of the intermediate and distal portions of the solid inner needle will deflect upon contact with a wall of the left atrium to prevent puncture of the left atrial wall,
    advancing the distal end of the outer needle through the atrial septum and into the left atrium;
    advancing the distal end of the sheath through the atrial septum and into the left atrium;
    withdrawing at least one of the needles from the left atrium; and
    introducing a flexible member via the lumen of the sheath to at least partially occlude the patent foramen ovale.

2. The method of claim 1, further comprising the step of using a locator device to stabilize the atrial septum prior to advancing the sharp tip of the inner needle through the septum.

3. The method of claim 1, further comprising the step of withdrawing the sheath from the left atrium.

4. The method of claim 1, wherein the flexible member is configured to reside within a lumen in a compressed state and configured to reside in an expanded state when outside the lumen, the method further including expanding the flexible member from a compressed stated to an expanded state.

5. The method of claim 4, further including the step of guiding the flexible member through the patent foramen ovale.

* * * * *